(12) United States Patent
Liu et al.

(10) Patent No.: US 12,221,640 B2
(45) Date of Patent: Feb. 11, 2025

(54) METHOD FOR PROMOTING N-ACETYLGLUCOSAMINE SYNTHESIS BY USING GlcN6P RESPONSIVE ELEMENT

(71) Applicant: JIANGNAN UNIVERSITY, Wuxi (CN)

(72) Inventors: Long Liu, Wuxi (CN); Jian Chen, Wuxi (CN); Guocheng Du, Wuxi (CN); Yaokang Wu, Wuxi (CN); Taichi Chen, Wuxi (CN); Jianghua Li, Wuxi (CN)

(73) Assignee: JIANGNAN UNIVERSITY, Jiangsu (CN)

( * ) Notice: Subject to any disclaimer, the term of this patent is extended or adjusted under 35 U.S.C. 154(b) by 995 days.

(21) Appl. No.: 17/279,271

(22) PCT Filed: Nov. 26, 2019

(86) PCT No.: PCT/CN2019/120949
§ 371 (c)(1),
(2) Date: Mar. 24, 2021

(87) PCT Pub. No.: WO2021/102682
PCT Pub. Date: Jun. 3, 2021

(65) Prior Publication Data
US 2022/0049280 A1    Feb. 17, 2022

(51) Int. Cl.
| | | |
|---|---|---|
| *C12P 19/26* | (2006.01) | |
| *C12N 9/10* | (2006.01) | |
| *C12N 9/22* | (2006.01) | |
| *C12N 15/67* | (2006.01) | |
| *C12N 15/75* | (2006.01) | |

(52) U.S. Cl.
CPC ............ *C12P 19/26* (2013.01); *C12N 9/1029* (2013.01); *C12N 15/67* (2013.01); *C12N 15/75* (2013.01); *C12Y 203/01004* (2013.01); *C12N 9/22* (2013.01)

(58) Field of Classification Search
None
See application file for complete search history.

(56) References Cited

U.S. PATENT DOCUMENTS 10,633,658 B2 *  4/2020  Liu .................... C12N 15/113

FOREIGN PATENT DOCUMENTS

| CN | 104498394 A | 4/2015 |
| CN | 107604025 A | 1/2018 |
| CN | 108148797 A | 6/2018 |
| CN | 110184229 A | 8/2019 |
| WO | 2018122225 A1 | 7/2018 |

OTHER PUBLICATIONS

Gaugué, I., Oberto, J. and Plumbridge, J. (2014), Binding of NagR and GamR to their DNA targets. Molecular Microbiology, 92: 100-115. (Year: 2014).*
Yanfeng Liu et al., "Modular pathway engineering of Bacillus subtilis for improved N-acetylglucosamine production" Metabolic Engineering 23 (2014) 42-52 (Feb. 19, 2014).
Isabelle Gaugue et al., "Regulation of amino sugar utilization in Bacillus subtilis by the GntR family regulators, NagR and GamR" Molecular Microbiology (2014) 92(1), 100-115 (Mar. 5, 2014).
Yang Gu et al., "Progress and prospect in microbial metabolic engineering" Bio Business Technology Jan. 2017 pp. 64-70 (Jan. 31, 2017).

* cited by examiner

*Primary Examiner* — Neil P Hammell
*Assistant Examiner* — Khaleda B Hasan
(74) *Attorney, Agent, or Firm* — SZDC Law PC

(57) ABSTRACT

The present invention provides a method for promoting N-acetylglucosamine synthesis by using the GlcN6P responsive element. In the present invention, *Bacillus subtilis* BSGNY-$P_{veg}$-glmS-$P_{43}$-GNA1 is used as a starting strain, in which a CRISPRi system regulated by GlcN6P responsive element is integrated into the genome to dynamically weaken the N-acetylglucosamine synthesis competitive pathway; a GlcN6P responsive promoter is used to regulate the expression of GNA1 on the plasmid to dynamically regulate the N-acetylglucosamine synthesis pathway; and the key gene alsSD involved in the acetoin synthesis pathway is knocked out. During fed-batch fermentation with this strain in a 15 L fermenter, the production of N-acetylglucosamine reaches 131.6 g/L and no by-product acetoin is accumulated, which lays a foundation for the production of GlcNAc by industrial fermentation.

13 Claims, 5 Drawing Sheets

Specification includes a Sequence Listing.

SEQUENCE LISTING

```
<160> NUMBER OF SEQ ID NOS: 36

<210> SEQ ID NO 1
<211> LENGTH: 5755
<212> TYPE: DNA
<213> ORGANISM: Artifical sequence
<220> FEATURE:
<223> OTHER INFORMATION: Vector pSTg-GNA1

<400> SEQUENCE: 1
ttcaccggtc caagaattgg agccaatcaa ttcttgcgga gaactgtgaa tgcgcaaacc    60
```

| | |
|---|---|
| aaccetttggc agaacatatc catcgcgtcc gccatctcca gcagccgcac gcggcgcatc | 120 |
| tcgggccgcg ttgctggcgt ttttccatag gctccgcccc cctgacgagc atcacaaaaa | 180 |
| tcgacgctca agtcagaggt ggcgaaaccc gacaggacta taaagatacc aggcgtttcc | 240 |
| ccctggaagc tccctcgtgc gctctcctgt tccgaccctg ccgcttaccg gatacctgtc | 300 |
| cgcctttctc ccttcgggaa gcgtggcgct ttctcatagc tcacgctgta ggtatctcag | 360 |
| ttcggtgtag tcgttcgct ccaagctggg ctgtgtgcac gaaccccccg ttcagcccga | 420 |
| ccgctgcgcc ttatccggta actatcgtct tgagtccaac ccggtaagac acgacttatc | 480 |
| gccactggca gcagccactg gtaacaggat tagcagagcg aggtatgtag gcggtgctac | 540 |
| agagttcttg aagtggtggc ctaactacgg ctacactaga aggacagtat ttggtatctg | 600 |
| cgctctgctg aagccagtta ccttcggaaa aagagttggt agctcttgat ccggcaaaca | 660 |
| aaccaccgct ggtagcggtg gttttttgt ttgcaagcag cagattacgc gcagaaaaaa | 720 |
| aggatctcaa gaagatcctt tgatcttttc tacgggtct gacgctcagt ggaacgaaaa | 780 |
| ctcacgttaa gggattttgg tcatgagatt atcaaaaagg atcttcacct agatcctttt | 840 |
| aaattaaaaa tgaagtttta atcaatcta aagtatatat gagtaaactt ggtctgacag | 900 |
| ttaccaatgc ttaatcagtg aggcacctat ctcagcgatc tgtctatttc gttcatccat | 960 |
| agttgcctga ctccccgtcg tgtagataac tacgatacgg gagggcttac catctggccc | 1020 |
| cagtgctgca atgataccgc gagacccacg ctcaccggct ccagatttat cagcaataaa | 1080 |
| ccagccagcc ggaagggccg agcgcagaag tggtcctgca actttatccg cctccatcca | 1140 |
| gtctattaat tgttgccggg aagctagagt aagtagttcg ccagttaata gtttgcgcaa | 1200 |
| cgttgttgcc attgctgcag gcatcgtggt gtcacgctcg tcgtttggta tggcttcatt | 1260 |
| cagctccggt tcccaacgat caaggcgagt tacatgatcc cccatgttgt gcaaaaaagc | 1320 |
| ggttagctcc ttcggtcctc cgatcgttgt cagaagtaag ttggccgcag tgttatcact | 1380 |
| catggttatg gcagcactgc ataattctct tactgtcatg ccatccgtaa gatgcttttc | 1440 |
| tgtgactggt gagtactcaa ccaagtcatt ctgagaatag tgtatgcggc gaccgagttg | 1500 |
| ctcttgcccg gcgtcaacac gggataatac cgcgccacat agcagaactt taaaagtgct | 1560 |
| catcattgga aaacgttctt cggggcgaaa actctcaagg atcttaccgc tgttgagatc | 1620 |
| cagttcgatg taacccactc gtgcacccaa ctgatcttca gcatctttta ctttcaccag | 1680 |
| cgtttctggg tgagcaaaaa caggaaggca aaatgccgca aaaagggaa taagggcgac | 1740 |
| acggaaatgt tgaatactca tactcttcct ttttcaatat tattgaagca tttatcaggg | 1800 |
| ttattgtctc atgagcggat acatatttga atgtatttag aaaaataaac aaataggggt | 1860 |
| tccgcgcaca tttccccgaa aagtgccacc tgacgtctaa gaaaccatta ttatcatgac | 1920 |
| attaacctat aaaaataggc gtatcacgag gccctttcgt cttcaagaat tcctgttata | 1980 |
| aaaaaaggat caatttgaa ctctctccca aagttgatcc cttaacgatt tagaaatccc | 2040 |
| tttgagaatg tttatataca ttcaaggtaa ccagccaact aatgacaatg attcctgaaa | 2100 |
| aaagtaataa caaattacta tacagataag ttgactgatc aacttccata ggtaacaacc | 2160 |
| tttgatcaag taagggtatg gataataaac cacctacaat tgcaatacct gttccctctg | 2220 |
| ataaaaagct ggtaaagtta agcaaactca ttccagcacc agcttcctgc tgtttcaagc | 2280 |
| tacttgaaac aattgttgat ataactgttt tggtgaacga aagcccacct aaaacaaata | 2340 |
| cgattataat tgtcatgaac catgatgttg tttctaaaag aaaggaagca gttaaaaagc | 2400 |
| taacagaaag aaatgtaact ccgatgttta acacgtataa aggacctctt ctatcaacaa | 2460 |

```
gtatcccacc aatgtagccg aaaataatga cactcattgt tccagggaaa ataattacac    2520
ttccgatttc ggcagtactt agctggtgaa catctttcat catataagga accatagaga    2580
caaaccctgc tactgttcca aatataattc ccccacaaag aactccaatc ataaaaggta    2640 tattttccc taatccggga tcaacaaaag gatctgttac tttcctgata tgttttacaa    2700
atatcaggaa tgacagcacg ctaacgataa gaaagaaat gctatatgat gttgtaaaca     2760
acataaaaaa tacaatgcct acagacatta gtataattcc tttgatatca aaatgacctt    2820
ttatccttac ttctttcttt aataatttca taagaaacgg aacagtgata attgttatca    2880
taggaatgag tagaagatag gaccaatgaa tataatgggc tatcattcca ccaatcgctg    2940
gaccgactcc ttctcccatg gctactatcg atccaataag accaaatgct ttacccctat    3000
tttcctttgg aatatagcgc gcaactacaa ccattacgag tgctggaaat gcagctgcac    3060
cagccccttg aataaaacga gccataataa gtaaggaaaa gaaagaatgg ccaacaaacc    3120
caattaccga cccgaaacaa tttattataa ttccaaatag gagtaacctt ttgatgccta    3180
attgatcaga tagctttcca tatacagctg ttccaatgga aaaggttaac ataaaggctg    3240
tgttcaccca gtttgtactc gcaggtggtt tattaaaatc atttgcaata tcaggtaatg    3300
agacgttcaa aaccatttca tttaatacgc taaaaaaaga taaaatgcaa agccaaatta    3360
aaatttggtt gtgtcgtaaa ttcgattgtg aataggatgt attcacattt caccctccaa    3420
taatgagggc agacgtagtt tatagggtta atgatacgct tccctctttt aattgaaccc    3480
tgttacattc attacacttc ataattaatt cctcctaaac ttgattaaaa cattttacca    3540
catataaact aagttttaaa ttcagtattt catcacttat acaacaatat ggcccgtttg    3600
ttgaactact cttaataaaa ataattttc cgttcccaat tccacattgc aataatagaa     3660
aatccatctt catcggcttt tcgtcatca tctgtatgaa tcaaatcgcc ttcttctgtg     3720
tcatcaaggt ttaattttt atgtatttct tttaacaaac caccatagga gattaacctt     3780
ttacggtgta aaccttcctc caaatcagac aaacgtttca aattcttttc ttcatcatcg    3840
gtcataaaat ccgtatcctt tacaggatat tttgcagttt cgtcaattgc cgattgtata    3900
tccgatttat atttattttt cggtcgaatc atttgaactt ttacatttgg atcatagtct    3960
aatttcattg ccttttttcca aaattgaatc cattgttttt gattcacgta gttttctgta    4020
ttcttaaaat aagttggttc cacacatacc aatacatgca tgtgctgatt ataagaatta    4080
tctttattat ttattgtcac ttccgttgca cgcataaaac caacaagatt tttattaatt    4140
tttttatatt gcatcattcg gcgaaatcct tgagccatat ctgacaaact cttatttaat    4200
tcttcgccat cataaacatt tttaactgtt aatgtgagaa acaaccaacg aactgttggc    4260
ttttgtttaa taacttcagc aacaaccttt tgtgactgaa tgccatgttt cattgctctc    4320
ctccagttgc acattggaca aagcctggat ttacaaaacc acactcgata caactttctt    4380
tcgcctgttt cacgattttg tttatactct aatatttcag cacaatcttt tactctttca    4440 gccttttttaa attcaagaat atgcagaagt tcaaagtaat caacattagc gattttctttt   4500 tctctccatg gtctcacttt tccactttt gtcttgtcca ctaaaaccct tgattttca     4560 tctgaataaa tgctactatt aggacacata atattaaaag aaaccccat ctatttagtt    4620 atttgtttgg tcacttataa ctttaacaga tggggttttt ctgtgcaacc aattttaagg    4680
gttttcaata ctttaaaaca catacatacc aacacttcaa cgcacctttc agcaactaaa    4740
ataaaaatga cgttatttct atatgtatca agataagaaa gaacaagttc aaaaccatca    4800
```

```
aaaaaagaca cctttcagg tgcttttttt attttataaa ctcattccct gatctcgact    4860
tcgttctttt tttacctctc ggttatgagt tagttcaaat tcgttctttt taggttctaa    4920
atcgtgtttt tcttggaatt gtgctgtttt atcctttacc ttgtctacaa accccttaaa    4980
aacgttttta aaggctttta agccgtctgt acgttcctta agatcaacgt gatataggtt    5040
tgctaacctt tgcgttcact taaggaatta gcttggtacg gatcccttt ataacaaatt    5100 ttcagaaatt aatattgaca gtttgataag ggcggtgcta aattcgtaat gacaagtatc    5160
ataaattggt cataacaaat atggtgcttg tctatctcag tgatagcggt accattatag    5220
gtaagagagg aatgtacaca tgcaccacca ccaccaccac agccatatct tcgacgcatc    5280
tgtactggct ccacatattc ctagtaacct tcctgataat ttcaaggtga gaccactggc    5340
aaaggatgat ttttcgaagg gatatgtcga cctgctgtca caattgacgt cagttggaaa    5400
ccttgaccaa gaagcatttg agaaacgatt tgaggcgatg agaacaagcg taccgaatta    5460
tcacatcgta gtaattgagg attccaacag ccagaaagtg gtggcgtctg ctagtttggt    5520
tgttgaaatg aaattcattc atggggccgg atcaaggggt cgtgttgaag atgttgtcgt    5580
cgatacagaa atgcgccggc aaaaattagg tgccgtgctt ttaaaaactt tggtgtcact    5640
tggcaaatct ttaggcgtct acaaaataag cctcgaatgc gtcccggaat tactcccgtt    5700
ctattcccaa tttggcttc aggatgactg taattttatg acccagcgct tttaa         5755
```

```
<210> SEQ ID NO 2
<211> LENGTH: 171
<212> TYPE: PRT
<213> ORGANISM: Artifical sequence
<220> FEATURE:
<223> OTHER INFORMATION: Glucosamine 6-phosphate N-acetyltransferase
      GNA1

<400> SEQUENCE: 2

Met His His His His His Ser His Ile Phe Asp Ala Ser Val Leu
1               5                   10                  15

Ala Pro His Ile Pro Ser Asn Leu Pro Asp Asn Phe Lys Val Arg Pro
            20                  25                  30

Leu Ala Lys Asp Asp Phe Ser Lys Gly Tyr Val Asp Leu Leu Ser Gln
        35                  40                  45

Leu Thr Ser Val Gly Asn Leu Asp Gln Glu Ala Phe Glu Lys Arg Phe
    50                  55                  60

Glu Ala Met Arg Thr Ser Val Pro Asn Tyr His Ile Val Val Ile Glu
65                  70                  75                  80

Asp Ser Asn Ser Gln Lys Val Val Ala Ser Ala Ser Leu Val Val Glu
                85                  90                  95

Met Lys Phe Ile His Gly Ala Gly Ser Arg Gly Arg Val Glu Asp Val
            100                 105                 110

Val Val Asp Thr Glu Met Arg Arg Gln Lys Leu Gly Ala Val Leu Leu
        115                 120                 125

Lys Thr Leu Val Ser Leu Gly Lys Ser Leu Gly Val Tyr Lys Ile Ser
    130                 135                 140

Leu Glu Cys Val Pro Glu Leu Leu Pro Phe Tyr Ser Gln Phe Gly Phe
145                 150                 155                 160

Gln Asp Asp Cys Asn Phe Met Thr Gln Arg Phe
                165                 170

<210> SEQ ID NO 3
<211> LENGTH: 9954
```

<212> TYPE: DNA
<213> ORGANISM: Artifical sequence
<220> FEATURE:
<223> OTHER INFORMATION: Vector pLCg-dCas9

<400> SEQUENCE: 3

```
tcgagttcat gtgcagctcc atcagcaaaa ggggatgata agtttatcac caccgactat      60
ttgcaacagt gccgttgatc gtgctatgat cgactgatgt catcagcggt ggagtgcaat     120
gtcatgaggg aagcggtgat cgccgaagta tcgactcaac tatcagaggt agttggcgtc     180
atcgagcgcc atctcgaacc gacgttgctg gccgtacatt tgtacggctc cgcagtggat     240
ggcggcctga agccacacag tgatattgat ttgctggtta cggtgaccgt aaggcttgat     300
gaaacaacgc ggcgagcttt gatcaacgac cttttggaaa cttcggcttc ccctggagag     360
agcgagattc tccgcgctgt agaagtcacc attgttgtgc acgacgacat cattccgtgg     420
cgttatccag ctaagcgcga actgcaattt ggagaatggc agcgcaatga cattcttgca     480
ggtatcttcg agccagccac gatcgacatt gatctggcta tcttgctgac aaaagcaaga     540
gaacatagcg ttgccttggt aggtccagcg gcggaggaac tctttgatcc ggttcctgaa     600
caggatctat ttgaggcgct aaatgaaacc ttaacgctat ggaactcgcc gcccgactgg     660
gctggcgatg agcgaaatgt agtgcttacg ttgtcccgca tttggtacag cgcagtaacc     720
ggcaaaatcg cgccgaagga tgtcgctgcc gactgggcaa tggagcgcct gccggcccag     780
tatcagcccg tcatacttga agctagacag gcttatcttg acaagaaga agatcgcttg     840
gcctcgcgcg cagatcagtt ggaagaattt gtccactacg tgaaaggcga gatcaccaag     900
gtagtcggca ataagatgc cgctcgccag tcgattggct gagctcatga agttcctatt     960
ccgaagttcc gcgaacgcgt aaaggatcta ggtgaagatc cttttttgata atctcatgac    1020
caaaatccct aacgtgagt tttcgttcca ctgagcgtca gaccccgtag aaaagatcaa    1080
aggatcttct tgagatcctt ttttctgcg cgtaatctgc tgcttgcaaa caaaaaaacc    1140
accgctacca gcggtggttt gtttgccgga tcaagagcta ccaactcttt ttccgaaggt    1200
aactggcttc agcagagcgc agataccaaa tactgtcctt ctagtgtagc cgtagttagg    1260
ccaccacttc aagaactctg tagcaccgcc tacatacctc gctctgctaa tcctgttacc    1320
agtggctgct gccagtggcg ataagtcgtg tcttaccggg ttggactcaa gacgatagtt    1380
accggataag gcgcagcggt cgggctgaac ggggggttcg tgcacacagc ccagcttgga    1440
gcgaacgacc tacaccgaac tgagatacct acagcgtgag ctatgagaaa gcgccacgct    1500
tcccgaaggg agaaaggcgg acaggtatcc ggtaagcggc agggtcggaa caggagagcg    1560
cacgagggag cttccagggg gaaacgcctg gtatctttat agtcctgtcg ggtttcgcca    1620
cctctgactt gagcgtcgat ttttgtgatg ctcgtcaggg gggcggagcc tatgaaaaaa    1680
cgccagcaac gcggccttt tacggttcct ggccttttgc tggccttttg ctcacatgtt    1740
ctttcctgcg ttatcccctg attctgtgga taaccgtatt accgcctttg agtgagctga    1800
taccgctcgc cgcagccgaa cgaccgagcg cagcgagtca gtgagcgagg aagcggaaga    1860
gcgcctgatg cggtattttc tccttacggg aattccatat ggattccgtg atgtcaaagc    1920
ttgaaaaaac gcacgtaaca aaagcaaaat ttatgctcca tgggggagac tacaaccccg    1980
atcagtggct ggatcggccc gatatttag ctgacgatat caaactgatg aagctttctc    2040
atacgaatac gttttctgtc ggcatttttg catggagcgc acttgagccg gaggagggcg    2100
tatatcaatt tgaatggctg gatgatattt ttgagcggat tcacagtata ggcggccggg    2160
```

-continued

```
tcatattagc aacgccgagc ggagcccgtc cggcctggct gtcgcaaacc tatccggaag    2220
ttttgcgcgt caatgcctcc cgcgtcaaac agctgcacgg cggaaggcac aaccactgcc    2280
tcacatctaa agtctaccga gaaaaaacac ggcacatcaa ccgcttatta gcagaacgat    2340
acggacatca cccggcgctg ttaatgtggc acatttcaaa cgaatacggg ggagattgcc    2400
actgtgattt atgccagcat gctttccggg agtggctgaa atcgaaatat gacaacagcc    2460
tcaagacatt gaaccatgcg tggtggaccc cttttggag  ccatacgttc aatgactggt    2520
cacaaattga aagcccttcg ccgatcggtg aaaatggctt gcatggcctg aatttagatt    2580
ggcgccggtt cgtcaccgat caaacgattt cgttttatga aaatgaaatc attccgctga    2640
aagaattgac gcctgatatc cctatcacaa cgaatttat  ggctgacaca ccggatttga    2700
tcccgtatac cgttcgtata gcatacatta tacgaagtta tgccatagtg actggcgatg    2760
ctgtcggaat ggacgatcgg caatagttac ccttattatc aagataagaa agaaaaggat    2820
ttttcgctac gctcaaatcc tttaaaaaaa cacaaaagac cacatttttt aatgtggtct    2880
tttattcttc aactaaagca cccattagtt caacaaacga aaattggata aagtgggata    2940
tttttaaaat atatatttat gttacagtaa tattgacttt taaaaaagga ttgattctaa    3000
tgaagaaagc agacaagtaa gcctcctaaa ttcactttag ataaaaattt aggaggcata    3060
tcaaatgaac tttaataaaa ttgatttaga caattggaag agaaaagaga tatttaatca    3120
ttatttgaac caacaaacga cttttagtat aaccacagaa attgatatta gtgttttata    3180
ccgaaacata aacaagaag  gatataaatt ttaccctgca tttatttct  tagtgacaag    3240
ggtgataaac tcaaatacag cttttagaac tggttacaat agcgacggag agttaggtta    3300
ttgggataag ttagagccac tttatacaat ttttgatggt gtatctaaaa cattctctgg    3360
tatttggact cctgtaaaga atgacttcaa agagttttat gatttatacc tttctgatgt    3420
agagaaatat aatggttcgg ggaaattgtt tcccaaaaca cctatacctg aaaatgcttt    3480
ttctcttcct attattccat ggacttcatt tactgggttt aacttaaata tcaataataa    3540
tagtaattac cttctaccca ttattacagc aggaaaattc attaataaag gtaattcaat    3600
atatttaccg ctatctttac aggtacatca ttctgttgt  gatggttatc atgcaggatt    3660
gtttatgaac tctattcagg aattgtcaga taggcctaat gactggcttt tataatatga    3720
gataatgccg actgtacttt ttacagtcgg ttttctaaaa cgatacatta ataggtacga    3780
aaaagcaact ttttttgcgc ttaaaaccag tcataccaat aaataacttc gtatagcata    3840
cattatacga acggtacgga attccgttaa ttcagaacag aaatccgcta tattgccaga    3900
ttggcaggat agcggatttt ctttttcta  ccttatgctt cagaacgctc ggttgccgcc    3960
gggcgttttt tatactagtg ccttatgaat gatatgactg ttctacgtg  aatttcgttc    4020
ggtctccccg tgtaataatt tgcgcatatt ccaccacttc ttcattttta tcataggtaa    4080
gggattctga taaaaacgca ggcgctccga cattggttaa taagtgtccg ctgatcgttt    4140
catccgttaa aatcggttcg atcgattccg tgccctgct  gatttcaata ttgtattttg    4200
tccttaacaa ttcaaacagc gagccggtgc attcctcctg cgccagcccc ggtgccgcct    4260
tccagggaat atatgaggta tgatactgca aaggttcccc ctcggcgtat ctgactctga    4320
caagcttgtt gacaggttca ttctctttca ttttcaaaag ctcggcgatg gaatgatcgg    4380
caggaatcac cacaagctca agcactttg  attcagaacg aagtcctctc atttgttctg    4440
caaagctcgt aatcttatgc ggaatcgcg  tttgtatttt ggccgccgat acaaatgtcc    4500
cttttccttg aattcttta  atatatccct caagctctag ctgctgcaga gccagtctca    4560
```

```
cagttgttct gctgacatca tattgttcgc aaaactcact ctccgtcggc agctgatcat    4620
tcgcctgata tttgcccgat ttaattaact caatgatttt aaacttgata acagaatata    4680
aagctgtcat ttcattctcc ccattctgta tgcaatccgt tcttttttcat tgagaccata   4740 ataccatttg ccctcccaat atgaaagatt tgtatccttc ttttataaca aattttcaga    4800
aatggaatta gcttggtacg gatccctttt ataacaatt ttcagaaatt aatattgaca     4860
gtttgataag ggcggtgcta aattcgtaat gacaagtatc ataaattggt cataacaaat    4920
atggtgcttg tctatctcgg taccctcgag aaaaggagga tgtacacatg gataagaaat    4980
actcaatagg cttagctatc ggcacaaata gcgtcggatg ggcggtgatc actgatgaat    5040
ataaggttcc gtctaaaaag ttcaaggttc tgggaaatac agaccgccac agtatcaaaa    5100
aaaatcttat aggggctctt ttatttgaca gtggagagac agcggaagcg actcgtctca    5160
aacggacagc tcgtagaagg tatacacgtc ggaagaatcg tatttgttat ctacaggaga    5220 tttttttcaaa tgagatggcg aaagtagatg atagtttctt tcatcgactt gaagagtctt    5280
ttttggtgga agaagacaag aagcatgaac gtcatcctat ttttggaaat atagtagatg    5340
aagttgctta tcatgagaaa tatccaacta tctatcatct gcgaaaaaaa ttggtagatt    5400
ctactgataa agcggatttg cgcttaatct atttggcctt agcgcatatg attaagtttc    5460
gtggtcattt tttgattgag ggagatttaa atcctgataa tagtgatgtg gacaaactat    5520
ttatccagtt ggtacaaacc tacaatcaat tatttgaaga aaaccctatt aacgcaagtg    5580
gagtagatgc taaagcgatt ctttctgcac gattgagtaa atcaagacga ttagaaaatc    5640
tcattgctca gctccccggt gagaagaaaa atggcttatt tgggaatctc attgctttgt    5700
cattgggttt gacccctaat tttaaatcaa attttgattt ggcagaagat gctaaattac    5760
agctttcaaa agatacttac gatgatgatt tagataattt attggcgcaa attggagatc    5820
aatatgctga tttgttttg gcagctaaga atttatcaga tgctatttta ctttcagata    5880
tcctaagagt aaatactgaa ataactaagg ctcccctatc agcttcaatg attaaacgct    5940
acgatgaaca tcatcaagac ttgactcttt taaaagcttt agttcgacaa caacttccag    6000
aaaagtataa agaaatcttt tttgatcaat caaaaacgg atatgcaggt tatattgatg     6060
ggggagctag ccaagaagaa ttttataaat ttatcaaacc aattttagaa aaaatggatg    6120
gtactgagga attattggtg aaactaaatc gtgaagattt gctgcgcaag caacggacct    6180
ttgacaacgg ctctattccc catcaaattc acttgggtga gctgcatgct attttgagaa    6240
gacaagaaga cttttatcca ttttttaaaag acaatcgtga aagattgaa aaaatcttga    6300 cttttcgaat tccttattat gttggtccat tggcgcgtgg caatagtcgt tttgcatgga    6360
tgactcggaa gtctgaagaa acaattaccc catggaattt tgaagaagtt gtcgataaag    6420
gtgcttcagc tcaatcattt attgaacgca tgacaaactt tgataaaaat cttccaaatg    6480
aaaaagtact accaaaacat agtttgcttt atgagtattt tacggtttat aacgaattga    6540
caaaggtcaa atatgttact gaaggaatgc gaaaaccagc atttctttca ggtgaacaga    6600
agaaagccat tgttgattta ctcttcaaaa caatcgaaa agtaaccgtt aagcaattaa    6660
aagaagatta tttcaaaaaa atagaatgtt ttgatagtgt tgaaatttca ggagttgaag    6720
atagatttaa tgcttcatta ggtacctacc atgatttgct aaaaattatt aaagataaag    6780
atttttggaa taatgaagaa aatgaagata tcttagagga tattgtttta acattgacct    6840
tatttgaaga tagggagatg attgaggaaa gacttaaaac atatgctcac ctctttgatg    6900
```

```
ataaggtgat gaaacagctt aaacgtcgcc gttatactgg ttggggacgt ttgtctcgaa    6960
aattgattaa tggtattagg gataagcaat ctggcaaaac aatattagat tttttgaaat    7020
cagatggttt tgccaatcgc aattttatgc agctgatcca tgatgatagt ttgacattta    7080
aagaagacat tcaaaaagca caagtgtctg acaaggcgaa tagtttacat gaacatattg    7140
caaatttagc tggtagccct gctattaaaa aaggtatttt acagactgta aaagttgttg    7200
atgaattggt caaagtaatg gggcggcata agccagaaaa tatcgttatt gaaatggcac    7260
gtgaaaatca gacaactcaa aagggccaga aaaattcgcg agagcgtatg aaacgaatcg    7320
aagaaggtat caaagaatta ggaagtcaga ttcttaaaga gcatcctgtt gaaaatactc    7380
aattgcaaaa tgaaaagctc tatctctatt atctccaaaa tggaagagac atgtatgtgg    7440
accaagaatt agatattaat cgtttaagtg attatgatgt cgatgccatt gttccacaaa    7500
gtttccttaa agacgattca atagacaata aggtcttaac gcgttctgat aaaaatcgtg    7560
gtaaatcgga taacgttcca agtgaagaag tagtcaaaaa gatgaaaaac tattggagac    7620
aacttctaaa cgccaagtta atcactcaac gtaagtttga taatttaacg aaagctgaac    7680
gtggaggttt gagtgaactt gataaagctg gttttatcaa cgccaattg gttgaaactc    7740
gccaaatcac taagcatgtg gcacaaattt tggatagtcg catgaatact aaatacgatg    7800
aaaatgataa acttattcga gaggttaaag tgattacctt aaaatctaaa ttagtttctg    7860
acttccgaaa agatttccaa ttctataaag tacgtgagat taacaattac catcatgccc    7920
atgatgcgta tctaaatgcc gtcgttggaa ctgctttgat taagaaatat ccaaaacttg    7980
aatcggagtt tgtctatggt gattataaag tttatgatgt tcgtaaaatg attgctaagt    8040
ctgagcaaga aataggcaaa gcaaccgcaa atatttctt ttactctaat atcatgaact    8100
tcttcaaaac agaaattaca cttgcaaatg gagagattcg caaacgccct ctaatcgaaa    8160
ctaatgggga aactggagaa attgtctggg ataaagggcg agattttgcc acagtgcgca    8220
aagtattgtc catgccccaa gtcaatattg tcaagaaaac agaagtacag acaggcggat    8280
tctccaagga gtcaatttta ccaaaaagaa attcggacaa gcttattgct cgtaaaaaag    8340
actgggatcc aaaaaatat ggtggttttg atagtccaac ggtagcttat tcagtcctag    8400
tggttgctaa ggtggaaaaa gggaaatcga agaagttaaa atccgttaaa gagttactag    8460
ggatcacaat tatggaaaga agttcctttg aaaaaaatcc gattgacttt ttagaagcta    8520
aaggatataa ggaagttaaa aaagacttaa tcattaaact acctaaatat agtctttttg    8580
agttagaaaa cggtcgtaaa cggatgctgg ctagtgccgg agaattacaa aaaggaaatg    8640
agctggctct gccaagcaaa tatgtgaatt ttttatattt agctagtcat tatgaaaagt    8700
tgaagggtag tccagaagat aacgaacaaa acaattgtt tgtggagcag cataagcatt    8760
atttagatga gattattgag caaatcagtg aattttctaa gcgtgttatt ttagcagatg    8820
ccaatttaga taaagttctt agtgcatata acaaacatag agacaaacca atacgtgaac    8880
aagcagaaaa tattattcat ttatttacgt tgacgaatct tggagctccc gctgctttta    8940
aatattttga taacaattt gatcgtaaac gatatacgtc tacaaaagaa gttttagatg    9000
ccactcttat ccatcaatcc atcactggtc tttatgaaac acgcattgat ttgagtcagc    9060
taggaggtga ctaactcgag taaggatctc caggcatcaa ataaaacgaa aggctcagtc    9120
gaaagactgg gcctttcgtt ttatctgttg tttgtcggtg aacgctctct actagagtca    9180
cactggctca ccttcgggtg ggcctttctg cgtttatacc tagggatata ttccgcttcc    9240
tcgctcactg cagcgtcatc acgaaagaac aagactttc accatataaa ctgctgatcg    9300
```

```
tcccgatgct gtatttaatc agcgaggaca ccgtttcccg tttaaaagcg tttacggctg    9360
acggcggcac cttagtcatg acgtatatca gcggggttgt gaatgagcat gacttaacat    9420
acacaggcgg atggcatccg gatcttcaag ctatatttgg agttgagcct cttgaaacgg    9480
acaccctgta tccgaaggat cgaaacgctg tcagctaccg cagccaaata tatgaaatga    9540
aggattatgc aaccgtgatt gatgtaaaga cagcttcagt ggaagcggtg tatcaagaag    9600
atttttatgc gcgcacgcca gcggtcacaa gccatgagta tcagcagggc aaggcgtatt    9660
ttatcggcgc gcgtttggag gatcaatttc agcgtgattt ctatgagggt ctgatcacag    9720
acctgtctct ctctccagtt tttccggttc ggcacgaaaa aggcgtctcc gtacaagcga    9780
ggcaggatca ggacaatgat tatattttg tcatgaattt cacggaagaa aaacagctgg    9840
tcacgtttga tcagagtgtg aaggacataa tgacaggaga catattgtca ggcgacctga    9900
cgatggaaaa gtatgaagtg agaattgtcg taaacacaca ttaggggta cccc            9954
```

<210> SEQ ID NO 4
<211> LENGTH: 3244
<212> TYPE: DNA
<213> ORGANISM: Artificial sequence
<220> FEATURE:
<223> OTHER INFORMATION: sgRNA expression fragment acting on glmM

<400> SEQUENCE: 4

```
ctttataagc ggattatgat tgtctttgcg gtaagcgata acccattctg cattaagctg      60
tatttggtcc attttttcgat aagtaacatc caaattaaat aatttttggg ccgaggaagg    120
aacaaatgtc ataccaattc cggcactgac taaaccaatc accatttgat attctgtggc    180
ttcctggaca atgttgggtc tgaagcccgc ttgttcacag aactgaataa atccatgta    240 tagagtaggc catgcttctt tagcaacagt aataattggt tcatctctta aatcctcaat    300
cgtaattgat tccttagaag tcaatgggtg ttgcttaggc aaagctaaaa cacaagggct    360
gctttgggcg gtttcgatat gtaaagctgt atgctgtaag ggaggatgaa gtataccaat    420
atcaatgttg ccctttagta gctcctcctg ctgcctagac gaggatattt cacgcagttc    480
tattttcaca gatgggaatt ttttacgata ttcccggaca atcggcggca gaaattcata    540
tgtagctgat ccgacaaaac cgattacgag aaggccttgc tcgccgcggg ccgtccgctg    600
tgccagttca attccttgtc cgatttgcat caatgccatg cggcaatgat ttaaaaagat    660
ttctcctgct gcggtaagct cgacaaatcg ttttgtcctt ttcagaagcg taactccgac    720
ttcttcctcc agctgtttga tctgctggct gagaggaggc tgcgtcatgt tcagccgccg    780
ggcagccttt ccgaaatgaa gctcttcggc tactgcgata agtattgaa gatggcgaag    840 ctccattcaa tatgcattcc tttccatagg ttaataattc gtattacata ttaatcataa    900
ggcgaatcga tattggaggt caatttccaa agagtgtata gtgaaactta tcacaagata    960
tttaaaattt tacgtttaaa atgcataata aggagtgagg gtgttacgaa ttcgagctcg   1020
gtacccgggg atcctctaga gattgtaccg ttcgtatagc atacattata cgaagttatc   1080
gattttcgtt cgtgaataca tgttataata actataacta ataacgtaac gtgactggca   1140
agagatattt ttaaaacaat gaataggttt acacttactt tagttttatg gaaatgaaag   1200
atcatatcat atataatcta gaataaaatt aactaaaata attattatct agataaaaaa   1260 tttgagaagcc aatgaaatct ataaataaac taaattaagt ttatttaatt aacaactatg   1320
gatataaaat aggtactaat caaaatagtg aggaggatat atttgaatac atacgaacaa   1380
```

```
attaataaag tgaaaaaaat acttcggaaa catttaaaaa ataaccttat tggtacttac    1440
atgtttggat caggagttga gagtggacta aaaccaaata gtgatcttga cttttagtc    1500 gtcgtatctg aaccattgac agatcaaagt aaagaaatac ttatacaaaa aattagacct    1560
atttcaaaaa aaataggaga taaaagcaac ttacgatata ttgaattaac aattattatt    1620
cagcaagaaa tggtaccgtg aatcatcct cccaaacaag aatttattta tggagaatgg    1680
ttacaagagc tttatgaaca aggatacatt cctcagaagg aattaaattc agatttaacc    1740
ataatgcttt accaagcaaa acgaaaaaat aaaagaatat acggaaatta tgacttagag    1800
gaattactac ctgatattcc attttctgat gtgagaagag ccattatgga ttcgtcagag    1860
gaattaatag ataattatca ggatgatgaa accaactcta tattaactttt atgccgtatg    1920 attttaacta tggacacggg taaaatcata ccaaaagata ttgcgggaaa tgcagtggct    1980
gaatcttctc cattagaaca tagggagaga atttttgttag cagttcgtag ttatcttgga    2040
gagaatattg aatggactaa tgaaaatgta aatttaacta taaactattt aaataacaga    2100
ttaaaaaaat tataaataac ttcgtatagc atacattata cgaacggtag aatcgtcgac    2160
ctgcaggcat gcaagcttgg cactggccgt caagaaaaaa agaaagcccc ttttagcagg    2220
gctttctttt tatttggctc ttttcctgat tttagataaa ataacatcaa aacagtaaag    2280
gtgtggtctg atgaaaatat tggttttggc agtgcatcct catatggaga cctcagttgt    2340
taataaggcg tgggctgagg aattgagtaa acatgcaaat atcacagtac gggatcttta    2400
taaggaatac ccggatgaag cgatagatgt tgcgaaggaa cagcagctgt gcgaggaata    2460
cgatcggatt gtctttcaat tcccgctata ttggtacagc tctccgccgc tcttgaaaaa    2520
atggcaggat cttgtgctga cttatggctg ggcttttggt tcagaaggaa atgccttgca    2580
tggcaaggag ctgatgctgg ctgtatcaac agggagcgaa gcggaaaaat atcaagcggg    2640
cggagcaaat cattactcga tcagtgagct attgaaacca tttcaggcca cgagtaatct    2700
gatcggcatg aagtatctgc ctccatatgt gttctatggc gtgaattatg cagctgcaga    2760
ggatatttct cacagtgcaa aacggttagc cgaatacatc cagcagcctt ttgtttaaaa    2820
tacagccctg tccaacatac ggcagggctg tatttgttta aaaatccggc agctcagaca    2880
ggttattttc cttgatgccg tccggttcac ttcgcaaaat gtcacgcccg tatttatgga    2940
agacatcaac atgagcgagt tttcctgatt ttgcttctga cagcgcagta gggtagtcga    3000
gctctcttcc tgtattggtt ttcactgcga taatattgtc ttcctcattt cttctaaccg    3060
caataatttc ttcttttcca gatggaacat tttcttgatc ggcagttgtt tgccgggctt    3120
tatacgattc atatgctgct tcaaattgat ccatatttac acctccgctt tttagcgtga    3180
acaaaaatgt cgatgatcat gtaaggtttc gacacagcat acgacaatat ttcctgagaa    3240
atat                                                                 3244
```

<210> SEQ ID NO 5
<211> LENGTH: 113
<212> TYPE: DNA
<213> ORGANISM: Artifical sequence
<220> FEATURE:
<223> OTHER INFORMATION: Promoter PgamA

<400> SEQUENCE: 5

```
cttttataac aaattttcag aaattaatat tgacagtttg ataagggcgg tgctaaattc      60
gtaatgacaa gtatcataaa ttggtcataa caaatatggt gcttgtctat ctc            113
```

```
<210> SEQ ID NO 6
<211> LENGTH: 114
<212> TYPE: DNA
<213> ORGANISM: Artifical sequence
<220> FEATURE:
<223> OTHER INFORMATION: GamR binding site

<400> SEQUENCE: 6
ttttgtcaaa ataattttat tgacaacgtc ttattaacgt tgatataatt taaattttat      60
ttgacaaaaa tgggctcgtg ttgtacaata aatgtcgtaa attggtcata acaa           114

<210> SEQ ID NO 7
<211> LENGTH: 97
<212> TYPE: DNA
<213> ORGANISM: Artifical sequence
<220> FEATURE:
<223> OTHER INFORMATION: GamR binding site

<400> SEQUENCE: 7
ttttgtcaaa ataattttat tgacaacgtc ttattaacgt tgatataatt taaattttat      60
ttgacataaa ttggtcataa caatacaata aatgtcg                              97

<210> SEQ ID NO 8
<211> LENGTH: 97
<212> TYPE: DNA
<213> ORGANISM: Artifical sequence
<220> FEATURE:
<223> OTHER INFORMATION: GamR binding site

<400> SEQUENCE: 8
ttttgtcaaa ataattttat tgacaacgtc ttattaacgt tgataaattg gtcataacaa      60
ttgacaaaaa tgggctcgtg ttgtacaata aatgtcg                              97

<210> SEQ ID NO 9
<211> LENGTH: 114
<212> TYPE: DNA
<213> ORGANISM: Artifical sequence
<220> FEATURE:
<223> OTHER INFORMATION: GamR binding site

<400> SEQUENCE: 9
ttttgtcaaa ataattttat tgacaacgtc ttattaacgt tgatataatt taaattttat      60
ttgacataaa ttggtcataa caatacaata aatgtcgtaa attggtcata acaa           114

<210> SEQ ID NO 10
<211> LENGTH: 114
<212> TYPE: DNA
<213> ORGANISM: Artifical sequence
<220> FEATURE:
<223> OTHER INFORMATION: GamR binding site

<400> SEQUENCE: 10
ttttgtcaaa ataattttat tgacaacgtc ttattaacgt tgataaattg gtcataacaa      60
ttgacaaaaa tgggctcgtg ttgtacaata aatgtcgtaa attggtcata acaa           114

<210> SEQ ID NO 11
<211> LENGTH: 97
<212> TYPE: DNA
<213> ORGANISM: Artifical sequence
<220> FEATURE:
<223> OTHER INFORMATION: GamR binding site

<400> SEQUENCE: 11
```
ttttgtcaaa ataattttat tgacaacgtc ttattaacgt tgataaattg gtcataacaa    60
ttgacataaa ttggtcataa caatacaata aatgtcg    97

<210> SEQ ID NO 12
<211> LENGTH: 114
<212> TYPE: DNA
<213> ORGANISM: Artifical sequence
<220> FEATURE:
<223> OTHER INFORMATION: GamR binding site

<400> SEQUENCE: 12
ttttgtcaaa ataattttat tgacaacgtc ttattaacgt tgataaattg gtcataacaa    60
ttgacataaa ttggtcataa caatacaata aatgtcgtaa attggtcata acaa    114

<210> SEQ ID NO 13
<211> LENGTH: 253
<212> TYPE: DNA
<213> ORGANISM: Artifical sequence
<220> FEATURE:
<223> OTHER INFORMATION: GamR binding site

<400> SEQUENCE: 13
cgagctttct taccttgacg gcagaaataa gctcgaagat tacgacatct taacattgat    60
gaaatactaa ggataaccgc ataacgaaaa agcactccat gtcagggtgc ttttttccta    120
ttgttttgca tttattttat ataatatttg gctatttgaa cttctgctct ttacatcttt    180 cgttttttc ttgtaaattc gtaatgacaa gtatcataaa ttggtcataa caaatatggt    240
gcttgtctat ctc    253

<210> SEQ ID NO 14
<211> LENGTH: 258
<212> TYPE: DNA
<213> ORGANISM: Artifical sequence
<220> FEATURE:
<223> OTHER INFORMATION: GamR binding site

<400> SEQUENCE: 14
tcaatatgtt ttcaaaagcc ggaaaagcgc tttcggacac cgtaaccaat actgcccagt    60
caatgtatga atggatacgg gatatgaatc aataagtacg tgaaagagaa aagcaaccca    120
gatatgatag ggaacttttc tctttcttgt tttacattga atctttacaa tcctattgat    180
ataatctaag ctagtgtata aattcgtaat gacaagtatc ataaattggt cataacaaat    240
atggtgcttg tctatctc    258

<210> SEQ ID NO 15
<211> LENGTH: 183
<212> TYPE: DNA
<213> ORGANISM: Artifical sequence
<220> FEATURE:
<223> OTHER INFORMATION: GamR binding site

<400> SEQUENCE: 15
aatgtttagt ggaaatgatt gcggcatccc gcaaaaaata ttgctgtaaa taaactggaa    60
tctttcggca tcccgcatga aacttttcac ccatttttcg ttgacaaaaa cattttcttc    120
atttaaattc gtaatgacaa gtatcataaa ttggtcataa caaatatggt gcttgtctat    180
ctc    183

<210> SEQ ID NO 16
<211> LENGTH: 183

<212> TYPE: DNA
<213> ORGANISM: Artifical sequence
<220> FEATURE:
<223> OTHER INFORMATION: GamR binding site

<400> SEQUENCE: 16
aatgtttagt ggaaatgatt gcggcatccc gcaaaaaata ttgctgtaaa taaactggaa        60
tctttcggca tcccgcatga aacttttcac ccattttttcg ttgacaaaaa cattttttc       120 atttaaattc gtaatgacaa gtatcataaa ttggtcataa caaatatggt gcttgtctat      180
ctc                                                                     183

<210> SEQ ID NO 17
<211> LENGTH: 183
<212> TYPE: DNA
<213> ORGANISM: Artifical sequence
<220> FEATURE:
<223> OTHER INFORMATION: GamR binding site

<400> SEQUENCE: 17
aatgtttagt ggaaatgatt gcggcatccc gcaaaaaata ttgctgtaaa taaactggaa        60
tctttcggca tcccgcatga aacttttcac ccattttttcg ttgacataaa ttggtcataa      120
caataaattc gtaatgacaa gtatcataaa ttggtcataa caaatatggt gcttgtctat      180
ctc                                                                     183

<210> SEQ ID NO 18
<211> LENGTH: 200
<212> TYPE: DNA
<213> ORGANISM: Artifical sequence
<220> FEATURE:
<223> OTHER INFORMATION: GamR binding site

<400> SEQUENCE: 18
aatgtttagt ggaaatgatt gcggcatccc gcaaaaaata ttgctgtaaa taaactggaa        60
tctttcggca tcccgcatga aacttttcac ccattttttcg taaattggtc ataacaattg      120
acaaaaacat ttttttcatt taaattcgta atgacaagta tcataaattg gtcataacaa      180
atatggtgct tgtctatctc                                                   200

<210> SEQ ID NO 19
<211> LENGTH: 200
<212> TYPE: DNA
<213> ORGANISM: Artifical sequence
<220> FEATURE:
<223> OTHER INFORMATION: GamR binding site

<400> SEQUENCE: 19
aatgtttagt ggaaatgatt gcggcatccc gcaaaaaata ttgctgtaaa taaactggaa        60
tctttcggca tcccgcatga aacttttcac ccattttttcg taaattggtc ataacaattg      120
acataaattg gtcataacaa taaattcgta atgacaagta tcataaattg gtcataacaa      180
atatggtgct tgtctatctc                                                   200

<210> SEQ ID NO 20
<211> LENGTH: 4238
<212> TYPE: DNA
<213> ORGANISM: Artifical sequence
<220> FEATURE:
<223> OTHER INFORMATION: Vector psga-GFP

<400> SEQUENCE: 20

-continued

| | |
|---|---|
| tcgagttcat gtgcagctcc atcagcaaaa ggggatgata agtttatcac caccgactat | 60 |
| ttgcaacagt gccgttgatc gtgctatgat cgactgatgt catcagcggt ggagtgcaat | 120 |
| gtcatgaggg aagcggtgat cgccgaagta tcgactcaac tatcagaggt agttggcgtc | 180 |
| atcgagcgcc atctcgaacc gacgttgctg gccgtacatt tgtacggctc cgcagtggat | 240 |
| ggcggcctga agccacacag tgatattgat ttgctggtta cggtgaccgt aaggcttgat | 300 |
| gaaacaacgc ggcgagcttt gatcaacgac cttttggaaa cttcggcttc ccctggagag | 360 |
| agcgagattc tccgcgctgt agaagtcacc attgttgtgc acgacgacat cattccgtgg | 420 |
| cgttatccag ctaagcgcga actgcaattt ggagaatggc agcgcaatga cattcttgca | 480 |
| ggtatcttcg agccagccac gatcgacatt gatctggcta tcttgctgac aaaagcaaga | 540 |
| gaacatagcg ttgccttggt aggtccagcg cggaggaaac tctttgatcc ggttcctgaa | 600 |
| caggatctat ttgaggcgct aaatgaaacc ttaacgctat ggaactcgcc gcccgactgg | 660 |
| gctggcgatg agcgaaatgt agtgcttacg ttgtcccgca tttggtacag cgcagtaacc | 720 |
| ggcaaaatcg cgccgaagga tgtcgctgcc gactgggcaa tggagcgcct gccggcccag | 780 |
| tatcagcccg tcatacttga agctagacag gcttatcttg acaagaaga gatcgcttg | 840 |
| gcctcgcgcg cagatcagtt ggaagaattt gtccactacg tgaaaggcga gatcaccaag | 900 |
| gtagtcggca aataagatgc cgctcgccag tcgattggct gagctcatga agttcctatt | 960 |
| ccgaagttcc gcgaacgcgt aaaggatcta ggtgaagatc ctttttgata atctcatgac | 1020 |
| caaaatccct taacgtgagt tttcgttcca ctgagcgtca daccccgtag aaaagatcaa | 1080 |
| aggatcttct tgagatcctt ttttttctgcg cgtaatctgc tgcttgcaaa caaaaaaacc | 1140 |
| accgctacca gcggtggttt gtttgccgga tcaagagcta ccaactcttt ttccgaaggt | 1200 |
| aactggcttc agcagagcgc agataccaaa tactgtcctt ctagtgtagc cgtagttagg | 1260 |
| ccaccacttc aagaactctg tagcaccgcc tacatacctc gctctgctaa tcctgttacc | 1320 |
| agtggctgct gccagtggcg ataagtcgtg tcttaccggg ttggactcaa gacgatagtt | 1380 |
| accggataag gcgcagcggt cgggctgaac ggggggttcg tgcacacagc ccagcttgga | 1440 |
| gcgaacgacc tacaccgaac tgagatacct acagcgtgag ctatgagaaa gcgccacgct | 1500 |
| tcccgaaggg agaaaggcgg acaggtatcc ggtaagcggc agggtcggaa caggagagcg | 1560 |
| cacgagggag cttccagggg gaaacgcctg gtatctttat agtcctgtcg ggtttcgcca | 1620 |
| cctctgactt gagcgtcgat ttttgtgatg ctcgtcaggg gggcggagcc tatggaaaaa | 1680 |
| cgccagcaac gcggccttt tacggttcct ggccttttgc tggccttttg ctcacatgtt | 1740 |
| ctttcctgcg ttatccctg attctgtgga taaccgtatt accgcctttg agtgagctga | 1800 |
| taccgctcgc cgcagccgaa cgaccgagcg cagcgagtca gtgagcgagg aagcggaaga | 1860 |
| gcgcctgatg cggtattttc tccttacgca tctgtgcggt atttcacacc gcatatgctg | 1920 |
| gatccgcgat gtttgcaaaa cgattcaaaa cctctttact gccgttattc gctggatttt | 1980 |
| tattgctgtt tcatttggtt ctggcaggac cggcggctgc gagtgctgaa acggcgaaca | 2040 |
| aatcgaatga gcttacagca ccgtcgatca aaagcggaac cattcttcat gcatggaatt | 2100 |
| ggtcgttcaa tacgttaaaa cacaatatga aggatattca tgatgcagga tatacagcca | 2160 |
| ttcagacatc tccgattaac caagtaaagg aagggaatca aggagataaa agcatgtcga | 2220 |
| actggtactg gctgtatcag ccgacatcgt atcaaattgg caaccgttac ttaggtactg | 2280 |
| aacaagaatt taagaaatg tgtgcagccg ctgaagaata tggcataaag gtcattgttg | 2340 |
| acgcggtcat caatcatacc accagtgatt atgccgcgat ttccaatgag gttaagagta | 2400 |

```
ttccaaactg gacacatgga aacacacaaa ttaaaaactg gtctgatcga tgggatgtca   2460
cgcagaacat gccatggcat gagattctac cgttcgtata gcatacatta tacgaagtta   2520
tcttgatatg gcttttata tgtgttactc tacatacaga aaggaggaac taaatatggc    2580
caagttgacc agtgccgttc cggtgctcac cgcgcgcgac gtcgccggag cggtcgagtt   2640
ctggaccgac cggctcgggt ctcccggga cttcgtggag gacgacttcg ccggtgtggt    2700
ccgggacgac gtgaccctgt tcatcagcgc ggtccaggac caggtggtgc cggacaacac   2760
cctggcctgg gtgtgggtgc gcggcctgga cgagctgtac gccgagtggt cggaggtcgt   2820
gtccacgaac ttccgggacg cctccggcc ggccatgacc gagatcggcg agcagccgtg    2880
ggggcgggag ttcgccctgc gcgacccggc cggcaactgc gtgcacttcg tggccgagga   2940
gcaggactga ataacttcgt atagcataca ttatacgaac ggtaaatcgt cgacctgcag   3000
gcttattaac gttgatataa tttaaatttt atttgacaaa aatgggctcg tgttgtacaa   3060
taaatgtaca agtgttggcc aaggaacgtt ttagagctag aaatagcaag ttaaaataag   3120
gctagtccgt tatcaacttg aaaaagtggc accgagtcgg tgcttttttt gaattccgtc   3180
gacatggatg agcgatgatg atatccgttt aggctgggcg gtgatagctt ctcgttcagg   3240
cagtacgcct ctttctttt ccagacctga gggaggcgga aatggtgtga ggttcccggg    3300
gaaaagccaa ataggcgatc gcgggagtgc tttatttgaa gatcaggcta tcactgcggt   3360
caatagattt cacaatgtga tggctggaca gcctgaggaa ctctcgaacc cgaatggaaa   3420
caaccagata tttatgaatc agcgcggctc acatggcgtt gtgctggcaa atgcaggttc   3480
atcctctgtc tctatcaata cggcaacaaa attgcctgat ggcaggtatg acaataaagc   3540
tggagcgggt tcatttcaag tgaacgatgg taaactgaca ggcacgatca atgccaggtc   3600
tgtagctgtg ctttatcctg atgatattgc aaaagcgcct catgttttcc ttgagaatta   3660
caaaacaggt gtaacacatt ctttcaatga tcaactgacg attaccttgc gtgcagatgc   3720
gaatacaaca aaagccgttt atcaaatcaa taatggacca gagacggcgt ttaaggatgg   3780
agatcaattc acaatcggaa aaggagatcc atttggcaaa acatacacca tcatgttaaa   3840
aggaacgaac agtgatggtg taacgaggac cgagaaatac agttttgtta aaagagatcc   3900
agcgtcggcc aaaaccatcg gctatcaaaa tccgaatcat tggagccagg taaatgctta   3960
tatctataaa catgatggga gccgagtaat tgaattgacc ggatcttggc ctggaaaacc   4020
aatgactaaa aatgcagacg gaatttacac gctgacgctg cctgcggaca cggatacaac   4080
caacgcaaaa gtgattttta ataatggcag cgcccaagtg cccggtcaga atcagcctgg   4140
ctttgattac gtgctaaatg gtttatataa tgactcgggc ttaagcggtt ctcttcccca   4200
ttgacccaag cttagatcta ttaccctgtt atccctac                          4238
```

<210> SEQ ID NO 21
<211> LENGTH: 76
<212> TYPE: DNA
<213> ORGANISM: Artifical sequence
<220> FEATURE:
<223> OTHER INFORMATION: Promoter PgamA

<400> SEQUENCE: 21

```
cagaaattaa tattgacagt ttgataaggg cggtgctaaa ttcgtaatga caagtatcat   60
aaattggtca taacaa                                                  76
```

<210> SEQ ID NO 22

```
<211> LENGTH: 60
<212> TYPE: DNA
<213> ORGANISM: Artifical sequence
<220> FEATURE:
<223> OTHER INFORMATION: Promoter Pveg

<400> SEQUENCE: 22
cgttgatata atttaaattt tatttgacaa aaatgggctc gtgttgtaca ataaatgtcg    60

<210> SEQ ID NO 23
<211> LENGTH: 77
<212> TYPE: DNA
<213> ORGANISM: Artifical sequence
<220> FEATURE:
<223> OTHER INFORMATION: Promoter Pvg1

<400> SEQUENCE: 23
cgttgatata atttaaattt tatttgacaa aaatgggctc gtgttgtaca ataaatgtcg    60
taaattggtc ataacaa                                                  77

<210> SEQ ID NO 24
<211> LENGTH: 60
<212> TYPE: DNA
<213> ORGANISM: Artifical sequence
<220> FEATURE:
<223> OTHER INFORMATION: Promoter Pvg2

<400> SEQUENCE: 24
cgttgatata atttaaattt tatttgacat aaattggtca taacaataca ataaatgtcg    60

<210> SEQ ID NO 25
<211> LENGTH: 60
<212> TYPE: DNA
<213> ORGANISM: Artifical sequence
<220> FEATURE:
<223> OTHER INFORMATION: Promoter Pvg3

<400> SEQUENCE: 25
cgttgataaa ttggtcataa caattgacaa aaatgggctc gtgttgtaca ataaatgtcg    60

<210> SEQ ID NO 26
<211> LENGTH: 77
<212> TYPE: DNA
<213> ORGANISM: Artifical sequence
<220> FEATURE:
<223> OTHER INFORMATION: Promoter Pvg4

<400> SEQUENCE: 26
cgttgatata atttaaattt tatttgacat aaattggtca taacaataca ataaatgtcg    60
taaattggtc ataacaa                                                  77

<210> SEQ ID NO 27
<211> LENGTH: 77
<212> TYPE: DNA
<213> ORGANISM: Artifical sequence
<220> FEATURE:
<223> OTHER INFORMATION: Promoter Pvg5

<400> SEQUENCE: 27
cgttgataaa ttggtcataa caattgacaa aaatgggctc gtgttgtaca ataaatgtcg    60
taaattggtc ataacaa                                                  77

<210> SEQ ID NO 28
<211> LENGTH: 60
```

<212> TYPE: DNA
<213> ORGANISM: Artifical sequence
<220> FEATURE:
<223> OTHER INFORMATION: Promoter Pvg6

<400> SEQUENCE: 28
cgttgataaa ttggtcataa caattgacat aaattggtca taacaataca ataaatgtcg    60

<210> SEQ ID NO 29
<211> LENGTH: 77
<212> TYPE: DNA
<213> ORGANISM: Artifical sequence
<220> FEATURE:
<223> OTHER INFORMATION: Promoter Pvg7

<400> SEQUENCE: 29
cgttgataaa ttggtcataa caattgacat aaattggtca taacaataca ataaatgtcg    60
taaattggtc ataacaa                                                   77

<210> SEQ ID NO 30
<211> LENGTH: 78
<212> TYPE: DNA
<213> ORGANISM: Artifical sequence
<220> FEATURE:
<223> OTHER INFORMATION: Promoter Prg

<400> SEQUENCE: 30
ttgaacttct gctctttaca tctttcgttt ttttcttgta aattcgtaat gacaagtatc    60
ataaattggt cataacaa                                                  78

<210> SEQ ID NO 31
<211> LENGTH: 79
<212> TYPE: DNA
<213> ORGANISM: Artifical sequence
<220> FEATURE:
<223> OTHER INFORMATION: Promoter Plg

<400> SEQUENCE: 31
aatctttaca atcctattga tataatctaa gctagtgtat aaattcgtaa tgacaagtat    60
cataaattgg tcataacaa                                                 79

<210> SEQ ID NO 32
<211> LENGTH: 183
<212> TYPE: DNA
<213> ORGANISM: Artifical sequence
<220> FEATURE:
<223> OTHER INFORMATION: Promoter Pvg

<400> SEQUENCE: 32
aatgtttagt ggaaatgatt gcggcatccc gcaaaaaata ttgctgtaa ataaactggaa    60 tctttcggca tcccgcatga aacttttcac ccattttttcg ttgacaaaa acatttttttc   120 atttaaattc gtaatgacaa gtatcataaa ttggtcataa caaatatgg tgcttgtctat   180 ctc                                                                  183

<210> SEQ ID NO 33
<211> LENGTH: 79
<212> TYPE: DNA
<213> ORGANISM: Artifical sequence
<220> FEATURE:
<223> OTHER INFORMATION: Promoter Psg

<400> SEQUENCE: 33

```
tttcacccat ttttcgttga caaaaacatt tttttcattt aaattcgtaa tgacaagtat      60
cataaattgg tcataacaa                                                  79

<210> SEQ ID NO 34
<211> LENGTH: 79
<212> TYPE: DNA
<213> ORGANISM: Artifical sequence
<220> FEATURE:
<223> OTHER INFORMATION: Promoter Psg1

<400> SEQUENCE: 34
tttcacccat ttttcgttga cataaattgg tcataacaat aaattcgtaa tgacaagtat      60
cataaattgg tcataacaa                                                  79

<210> SEQ ID NO 35
<211> LENGTH: 80
<212> TYPE: DNA
<213> ORGANISM: Artifical sequence
<220> FEATURE:
<223> OTHER INFORMATION: Promoter Psg2

<400> SEQUENCE: 35
taaattggtc ataacaattg acaaaaacat tttttcatt taaattcgta atgacaagta       60
tcataaattg gtcataacaa                                                 80

<210> SEQ ID NO 36
<211> LENGTH: 80
<212> TYPE: DNA
<213> ORGANISM: Artifical sequence
<220> FEATURE:
<223> OTHER INFORMATION: Promoter Psg3

<400> SEQUENCE: 36
taaattggtc ataacaattg acataaattg gtcataacaa taaattcgta atgacaagta      60
tcataaattg gtcataacaa                                                 80
```

METHOD FOR PROMOTING N-ACETYLGLUCOSAMINE SYNTHESIS BY USING GlcN6P RESPONSIVE ELEMENT

This application is the National Stage Application of PCT/CN2019/120949, filed on Nov. 26, 2019, which is incorporated by reference for all purposes as if fully set forth herein.

FIELD OF THE INVENTION

The present invention relates to the technical field of genetic engineering, and more particularly to a method for promoting N-acetylglucosamine synthesis by using GlcN6P responsive element.

DESCRIPTION OF THE RELATED ART

Acetylglucosamine is a monosaccharide in organisms, which is widely found in bacteria, yeasts, molds, plants, and animals. In the human body, acetylglucosamine is a precursor for synthesizing the disaccharide units of glycosaminoglycan, which plays an important role in repairing and maintaining cartilage and joint functions. Therefore, acetylglucosamine is widely used as a medicine and nutrient supplement to treat and repair joint damage. In addition, acetylglucosamine is also widely used in the cosmetics field. At present, acetylglucosamine is mainly produced by acid hydrolysis of chitin in shrimp shells or crab shells. The waste liquid produced by this method causes serious environmental pollution, and the obtained product is likely to cause allergic reactions and thus not suitable for consumption by those with seafood allergies.

Bacillus subtilis is a widely used host for producing enzyme preparations for use in food and important nutritional chemicals. Its products have been approved by the FDA as the "generally regarded as safe"(GRAS) safety level. Therefore, the use of metabolic engineering to construct recombinant Bacillus subtilis is an effective way to produce acetylglucosamine at the food safety level. When N-acetylglucosamine is synthesized with glucose as a substrate, the glycolysis pathway, the pentose phosphate pathway, and the peptidoglycan synthesis pathway compete for the glucose that enters the cells, thus limiting the efficient synthesis of N-acetylglucosamine. Patent Application Publication No. CN108148797A provides a recombinant Bacillus subtilis (BSGNX-dCas9-zpg), in which these three competitive pathways are weakened by the xylose-induced CRISPRi system, so that the yield of and rate of conversion of the substrate into N-acetylglucosamine reach a high level; and after the engineering, the catabolite repression is eliminated, such that glucose and xylose could be used together. However, xylose is much more expensive than glucose. Its use in fermentation and production will increase the production cost, and the addition of an inducing agent will make the fermentation operations complicated. Therefore, the recombinant Bacillus subtilis needs to be further engineered, so that it can automatically adjust the related metabolic network when glucose is used as the carbon source alone, and can efficiently synthesize N-acetylglucosamine.

Therefore, a low-cost and high-efficiency method for synthesizing N-acetylglucosamine is provided, which has simple operations and requires no addition of an inducing agent, and thus is of great significance for the industrial application of N-acetylglucosamine.

SUMMARY OF THE INVENTION

To solve the problems of "complicated operations caused by the addition of an inducing agent during the fermentation process and increased production cost caused by the addition of xylose", in the present invention, recombinant Bacillus subtilis is used to continuously and efficiently synthesize N-acetylglucosamine with glucose as the sole carbon source.

The first object of the present invention is to provide a method for promoting N-acetylglucosamine synthesis, which comprises controlling the expression of glucosamine 6-phosphate N-acetyltransferase GNA1 by using a GlcN6P responsive element to dynamically regulate the N-acetylglucosamine synthesis pathway; and using the GlcN6P responsive element to regulate a compound formed by binding the expressed dCas9 protein to three sgRNA expression fragments acting on zwf, pfkA and glmMgenes, to dynamically weaken the glycolysis pathway, the pentose phosphate pathway and the peptidoglycan synthesis pathway. The GlcN6P responsive element includes the transcription factor GamR of Bacillus subtilis and a promoter containing a GamR binding site, where the promoter is a $P_{gamA}$ promoter or a hybrid promoter constructed by adding a GamR binding site to a constitutive promoter.

In an embodiment of the present invention, the transcription factor GamR has an amino acid sequence comprising positions 1-235 of an amino acid sequence deposited under NCBI Accession No.: WP_015382651.1.

In an embodiment of the present invention, the promoter $P_{gamA}$ has a nucleotide sequence as shown in SEQ ID NO: 5, and the constructed hybrid promoter comprises $P_{vg1}$, $P_{vg2}$, $P_{vg3}$, $P_{vg4}$, $P_{vg5}$, $P_{vg6}$, $P_{vg7}$, $P_{rg}$, $P_{lg}$, $P_{vg}$, $P_{sg}$, $P_{sg1}$, $P_{sg2}$, and $P_{sg3}$ having a nucleotide sequence respectively as shown in SEQ ID NO:6-SEQ ID NO:19.

In an embodiment of the present invention, the glucosamine 6-phosphate N-acetyltransferase GNA1 has an amino acid sequence as shown in SEQ ID NO: 2.

In an embodiment of the present invention, pSTg-GNA1 is used as an expression vector of the glucosamine 6-phosphate N-acetyltransferase GNA1, and the vector pSTg-GNA1 has a nucleotide sequence as shown in SEQ ID NO: 1. The promoter $P_{gamA}$ and a GNA1 coding gene are ligated to the vector pSTOP1622, to replace the repressor xylR and the promoter $P_{xylA}$ on the vector pSTOP1622. The construction method of the vector pSTOP1622 can be found in the literature: Biedendieck, R., Yang, Y, Deckwer, W. D., Malten, M., Jahn, D., 2007. Plasmid system for the intracellular production and purification of affinity-tagged proteins in Bacillus megaterium.Biotechnol.Bioeng. 96, 525-537.

In an embodiment of the present invention, the expression of GNA1 specifically includes transforming the free vector pSTg-GNA1 into Bacillus subtilis, and screening the transformant with tetracycline.

In an embodiment of the present invention, the dCas9 protein has an amino acid sequence as shown in SEQ ID NO: 1 in CN108148797A.

In an embodiment of the present invention, pLCg-dCas9 is used as an expression vector of dCas9 protein, and the vector pLCg-dCas9 has a nucleotide sequence as shown in SEQ ID NO:3. The dCas9 protein is obtained by replacing the repressor XylR and the xylose-inducible promoter on the vector pLCx-dCas9 (constructed according to a method as described in Patent Application Publication No. CN108148797A) with gamR and $P_{gamA}$. The vector pLCx-dCas9 comprises a chloramphenicol resistance gene for resistance screening upstream of $P_{gamA}$. An upstream and a downstream homologous arm of the lacA gene of Bacillus subtilis are respectively provided at two ends of chloramphenicol resistance gene-$P_{gamA}$-dCas9.

In an embodiment of the present invention, the expression of the dCas9 protein specifically includes transforming the pLCg-dCas9 vector linearized with the endonuclease Eco91I into the lacA site on the genome of *Bacillus subtilis* BSGNY-P$_{veg}$-glmS-P$_{43}$-GNA1.

In an embodiment of the present invention, the sgRNA expression fragment acting on zwf has a nucleotide sequence as shown in SEQ ID NO: 2 in Patent Publication No. CN108148797A; the sgRNA expression fragment acting on pfkA has a nucleotide sequence as shown in SEQ ID NO: 3 in Patent Publication No. CN108148797A; and the sgRNA expression fragment acting on glmM has a nucleotide sequence as shown in SEQ ID NO: 4 in Patent Publication No. CN108148797A.

In an embodiment of the present invention, the sgRNA expression fragment is integrated into the genome of recombinant *Bacillus subtilis* by transforming the linearized integration vector psga-zpg (constructed according to a method as described in Patent Publication No. CN108148797A). The vector psga-zpg has a nucleotide sequence as shown in SEQ ID NO: 7 in Patent Publication No. CN108148797A.

In an embodiment of the present invention, after the three sgRNA expression fragments acting on zwf, pfkA, and glmM genes are bound to dCas9, the glycolysis pathway, the pentose phosphate pathway, and the peptidoglycan synthesis pathway can be dynamically weakened by the CRISPRi mechanism. Specifically, the transcriptional sgRNA forms a compound with the dCas9 protein, which is then directed to recognize and bind to a genomic DNA that is specifically complementary to the sgRNA, to prevent the RNA polymerase from binding to the gene and inhibit the transcription of the gene, thereby realizing the weakening of the expression of a specific gene. Because the dCas9 protein is dynamically expressed by using the GlcN6P responsive element, the process of weakening is also dynamic. The specific principle of CRISPRi can be found in the literature: Gilbert L A, Larson M H, Morsut L, Liu Z, Brar G A, Torres S E, Stern-Ginossar N, Brandman O, Whitehead E H, Doudna J A, Lim W A, Weissman J S, Qi L S. 2013. CRISPR-mediated modular RNA-guided regulation of transcription in eukaryotes. Cell 154:442.

In an embodiment of the present invention, the sgRNA expression fragment is integrated into the amyE site on the genome of *Bacillus subtilis* BSGNY-P$_{veg}$-glmS-P$_{43}$-GNA1 by transforming the psga-zpg vector which is linearized with the endonuclease Eco91I.

In an embodiment of the present invention, the method further includes knocking out the key gene alsSD responsible for the synthesis of by-product acetoin in *Bacillus subtilis*.

In an embodiment of the present invention, the key gene alsSD involved in the acetoin synthesis pathway is knocked out by transforming an alsSD knockout frame having a nucleotide sequence as shown in SEQ ID NO: 4, which is obtained by fusing the upstream and downstream homologous arm of the alsSD gene to the spectinomycin resistance gene by fusion PCR.

In an embodiment of the present invention, the key gene responsible for the synthesis of by-product acetoin is knocked out specifically by the steps of amplifying each 1000 bp of the upstream and downstream homologous arm of the alsSD gene with the genome of *Bacillus subtilis* as a template; amplifying the spectinomycin resistance gene fragment with the p7S6 plasmid as a template; fusing the upstream and downstream homologous arm of the alsSD gene to the spectinomycin resistance gene by fusion PCR, to obtain a knockout frame; and transforming the knockout frame into *Bacillus subtilis*, and screening in a spectinomycin-containing plate. The p7S6 plasmid and detailed gene knockout method can be found in the literature: Yan X, Yu H J, Hong Q, Li S P. 2008. Cre/lox system and PCR-based genome engineering in *Bacillus subtilis*. Appl. Environ. Microbiol. 74:5556-5562.

A second object of the present invention is to provide a recombinant *Bacillus subtilis*, in which the GlcN6P responsive element is used to control the expression of glucosamine 6-phosphate N-acetyltransferase GNA1 to dynamically regulate the N-acetylglucosamine synthesis pathway; and the GlcN6P responsive element is also used to regulate a compound formed by binding the expressed dCas9 protein to three sgRNA expression fragments acting on zwf, pfkA and glmM genes, to dynamically weaken the glycolysis pathway, the pentose phosphate pathway and the peptidoglycan synthesis pathway. The GlcN6P responsive element includes the transcription factor GamR of *Bacillus subtilis* and a promoter containing a GamR binding site, where the transcription factor GamR has an amino acid sequence comprising positions 1-235 of an amino acid sequence deposited under NCBI Accession No.: WP_015382651.1, and the promoter is a P$_{gamA}$ promoter or a hybrid promoter constructed by adding a GamR binding site to a constitutive promoter.

A third object of the present invention is to provide a method for constructing the genetically engineered bacterium. In the method, *Bacillus subtilis* BSGNY-P$_{veg}$-glmS-P$_{43}$-GNA1 is used as a starting strain. The starting strain is based on *Bacillus subtilis* 168 (BS168) in which the genotype was engineered as follows: ΔnagPΔgamPΔgamAΔΔnagAΔΔnagBΔldhΔptaΔglcKΔpckΔΔ pyk::lox72. The promoter P$_{veg}$ is used to regulate the expression of the phosphatase yqaB from *E. coli* and the glmS of *Bacillus subtilis* 168, and the promoter P$_{43}$ is used to regulate the recombinant expression of GNA1 on the plasmid.

In an embodiment of the present invention, *Bacillus subtilis* BSGNY-P$_{veg}$-glmS-P$_{43}$-GNA1 is constructed according to a method as described in Patent Application Publication No. CN107699533A.

A fourth object of the present invention is to provide a method for producing acetylglucosamine, which comprises seed culture of the recombinant *Bacillus subtilis*, and further fermentation culture in a fermentation medium.

In an embodiment of the present invention, the method comprises inoculating the seed of the recombinant *Bacillus subtilis* stain cultured at 35-39° C. and 200-220 rpm for 10-15 h into a fermentation medium in a shake flask at an inoculation amount of 1-10%, and culturing at 35-39° C. and 200-220 rpm for 50-70 h.

In an embodiment of the present invention, the method comprises inoculating the seed cultured at 35-39° C. and 200-220 rpm for 10-15 h into a fermentation medium in a fermenter at an inoculation amount of 1-10%, and culturing in the fermenter with a liquid volume of 30-50% at 35-39° C. and pH 6.5-7.5, where the rate of aeration is 1-2 vvm, the rotational speed is controlled to 500-900 rpm to maintain dissolved oxygen at 30% or higher, and glucose of 750 g/L is continuously added to control the glucose concentration between 1-30 g/L.

The present invention also provides the use of the recombinant *Bacillus subtilis* or the method for promoting N-acetylglucosamine synthesis in the fields of food, pharmaceuticals, nutraceuticals, and health products, or cosmetics.

The present invention has the following beneficial effects.

(1) The present invention provides a method for constructing a GlcN6P responsive element, and a series of synthetic promoters that can be activated by intracellular GlcN6P are obtained. A method for efficiently synthesizing N-acetylglucosamine with glucose by using the responsive element is also achieved, in which the GlcN6P responsive element is used to regulate the N-acetylglucosamine synthesis pathway and its main competitive pathways (glycolysis pathway, pentose phosphate pathway, and peptidoglycan synthesis pathway), thereby promoting the continuous and efficient synthesis of N-acetylglucosamine; and the accumulation of by-products is further avoided by knocking out the synthesis pathway of by-product acetoin, thus further improving the production of N-acetylglucosamine.

(2) Acetylglucosamine can be continuously and efficiently synthesized by the recombinant *Bacillus subtilis* constructed in the present invention, with a production reaching 28.0 g/L in a shake flask, and reaching 131.6 g/L in a 15 L fermenter by fed-batch fermentation, which represents the highest level of fermentation production at present, and lays a foundation for its industrialization.

BRIEF DESCRIPTION OF THE DRAWINGS

FIG. 1A shows the catabolism-related genes of glucose (Glc), glucosamine (GlcN), and N-acetylglucosamine (GlcNAc) in *Bacillus subtilis*, FIG. 1B shows the regulation of catabolism-related genes of GlcN and GlcNAc by GlcN6P, and FIG. 1C shows the mechanism of regulation on promoter PgamA by GlcN6P.

FIG. 2A shows part of the sequence of promoters including a GamR binding site, and FIG. 2B shows the change in expression of these promoters before and after GamR binding.

Figure 2:
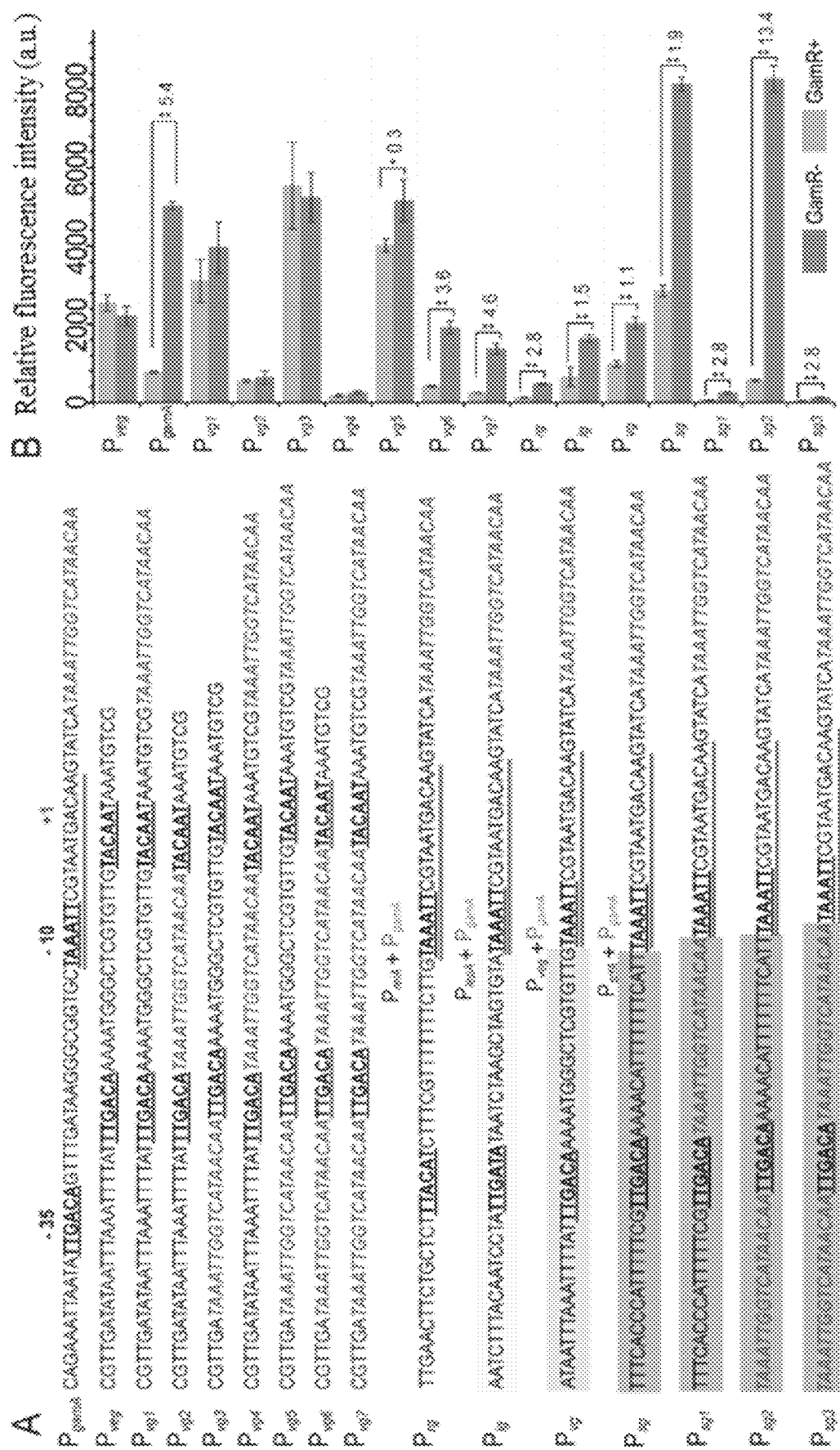
FIG. 2 shows the constructed GlcN6P responsive element.

The partial sequences of promoters shown in FIG. 2A are as follows.

$P_{gamA}$:
(SEQ ID NO: 21)
CAGAAATTAATATTGACAGTTTGATAAGGGCGGTGCTAAATTCGTAATG

ACAAGTATCATAAATTGGTCATAACAA $P_{veg}$:
(SEQ ID NO: 22)
CGTTGATATAATTTAAATTTTATTTGACAAAAATGGGCTCGTGTTGTAC

AATAAATGTCG $P_{vg1}$:
(SEQ ID NO: 23)
CGTTGATATAATTTAAATTTTATTTGACAAAAATGGGCTCGTGTTGTAC

AATAAATGTCGTAAATTGGTCATAACAA $P_{vg2}$:
(SEQ ID NO: 24)
CGTTGATATAATTTAAATTTTATTTGACATAAATTGGTCATAACAATAC

AATAAATGTCG $P_{vg3}$:
(SEQ ID NO: 25)
CGTTGATAAATTGGTCATAACAATTGACAAAAATGGGCTCGTGTTGTAC

AATAAATGTCG $P_{vg4}$:
(SEQ ID NO: 26)
CGTTGATATAATTTAAATTTTATTTGACATAAATTGGTCATAACAATAC

AATAAATGTCGTAAATTGGTCATAACAA $P_{vg5}$:
(SEQ ID NO: 27)
CGTTGATAAATTGGTCATAACAATTGACAAAAATGGGCTCGTGTTGTAC

AATAAATGTCGTAAATTGGTCATAACAA $P_{vg6}$:
(SEQ ID NO: 28)
CGTTGATAAATTGGTCATAACAATTGACATAAATTGGTCATAACAATAC

AATAAATGTCG $P_{vg7}$:
(SEQ ID NO: 29)
CGTTGATAAATTGGTCATAACAATTGACATAAATTGGTCATAACAATAC

AATAAATGTCGTAAATTGGTCATAACAA $P_{rg}$:
(SEQ ID NO: 30)
TTGAACTTCTGCTCTTTACATCTTTCGTTTTTTTCTTGTAAATTCGTAA

TGACAAGTATCATAAATTGGTCATAACAA $P_{lg}$:
(SEQ ID NO: 31)
AATCTTTACAATCCTATTGATATAATCTAAGCTAGTGTATAAATTCGTA

ATGACAAGTATCATAAATTGGTCATAACAA $P_{vg}$:
(SEQ ID NO: 32)
AATGTTTAGTGGAAATGATTGCGGCATCCCGCAAAAAATATTGCTGTAA

ATAAACTGGAATCTTTCGGCATCCCGCATGAAACTTTTCACCCATTTTT

CGTTGACAAAAACATTTTTTTCATTTAAATTCGTAATGACAAGTATCAT

AAATTGGTCATAACAAATATGGTGCTTGTCTATCTC $P_{sg}$:
(SEQ ID NO: 33)
TTTCACCCATTTTTCGTTGACAAAAACATTTTTTTCATTTAAATTCGTA

ATGACAAGTATCATAAATTGGTCATAACAA $P_{sg1}$:
(SEQ ID NO: 34)
TTTCACCCATTTTTCGTTGACATAAATTGGTCATAACAATAAATTCGTA

ATGACAAGTATCATAAATTGGTCATAACAA $P_{sg2}$:
(SEQ ID NO: 35)
TAAATTGGTCATAACAATTGACAAAAACATTTTTTTCATTTAAATTCGT

AATGACAAGTATCATAAATTGGTCATAACAA $P_{sg3}$:
(SEQ ID NO: 36)
TAAATTGGTCATAACAATTGACATAAATTGGTCATAACAATAAATTCGT

AATGACAAGTATCATAAATTGGTCATAACAA

Figure 3:
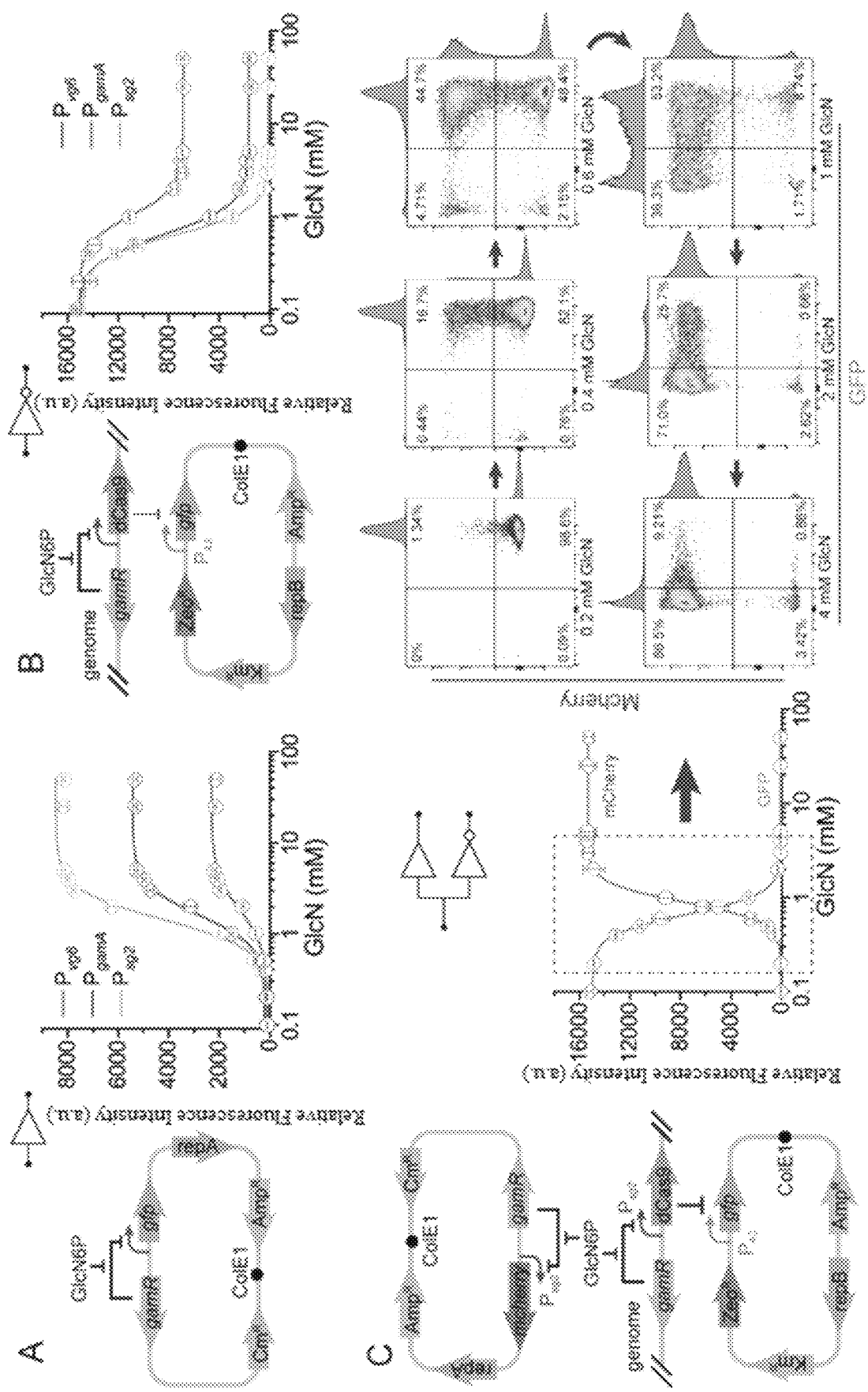

FIG. 3 shows the verification of the regulatory effect of the GlcN6P responsive element. FIG. 3A shows the activation verification, FIG. 3B shows the inhibition verification, and FIG. 3C shows the simultaneous activation and inhibition verification.

Figure 4:
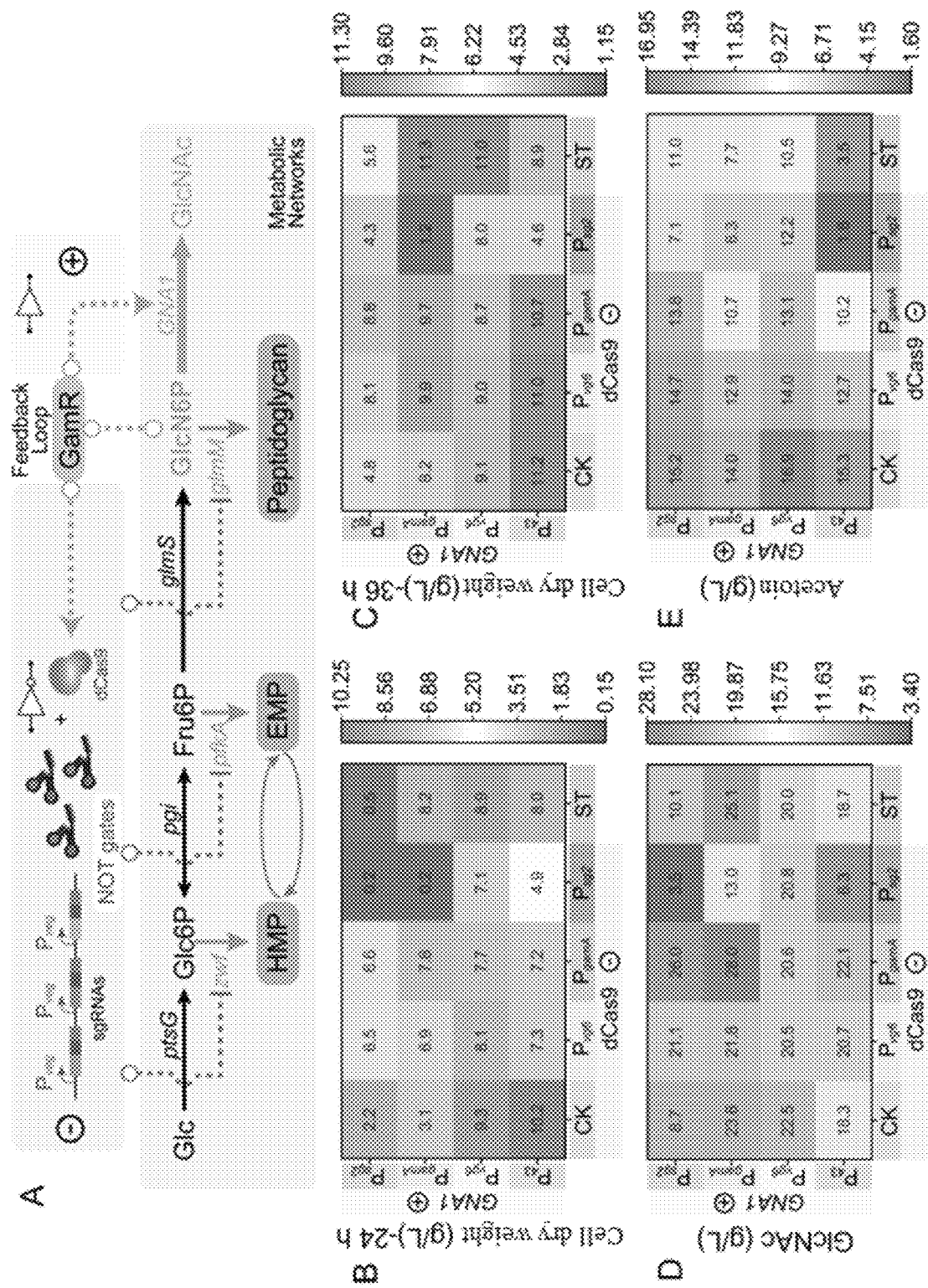

FIG. 4 shows the cell growth and product synthesis under the regulation of GlcN6P responsive element. FIG. 4A shows a process of regulation with the GlcN6P responsive element, FIG. 4B shows the dry weight of cells 24 h after regulation with the GlcN6P responsive element, FIG. 4C shows the dry weight of cells at 36 h, FIG. 4D shows the synthesis of GlcNAc, and FIG. 4E shows the synthesis of by-product acetoin.

Figure 5:
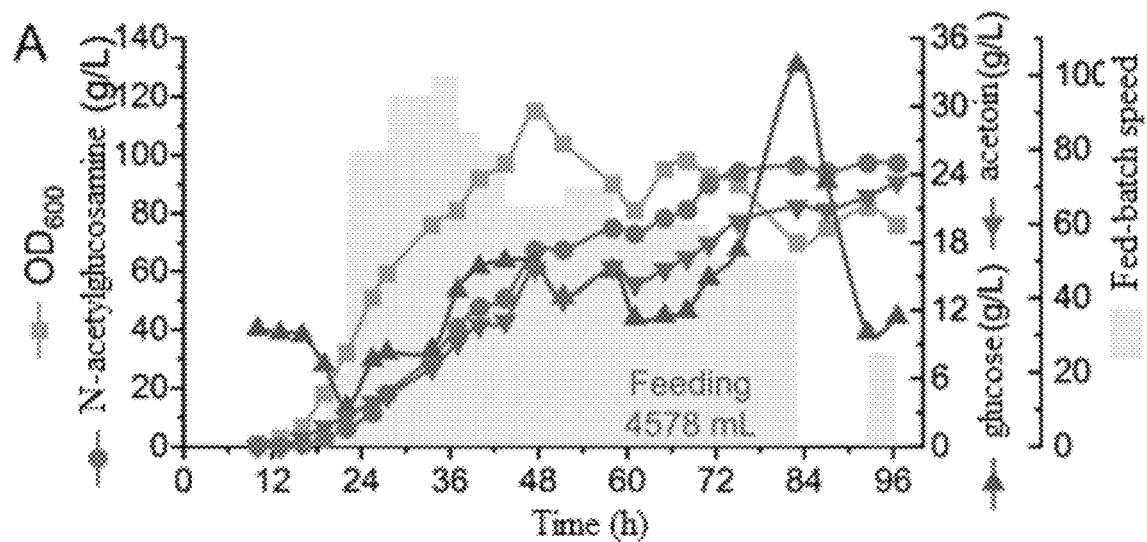

FIG. 5 shows the results of fed-batch fermentation in a 15 L tank with BNDR022.

Figure 6:
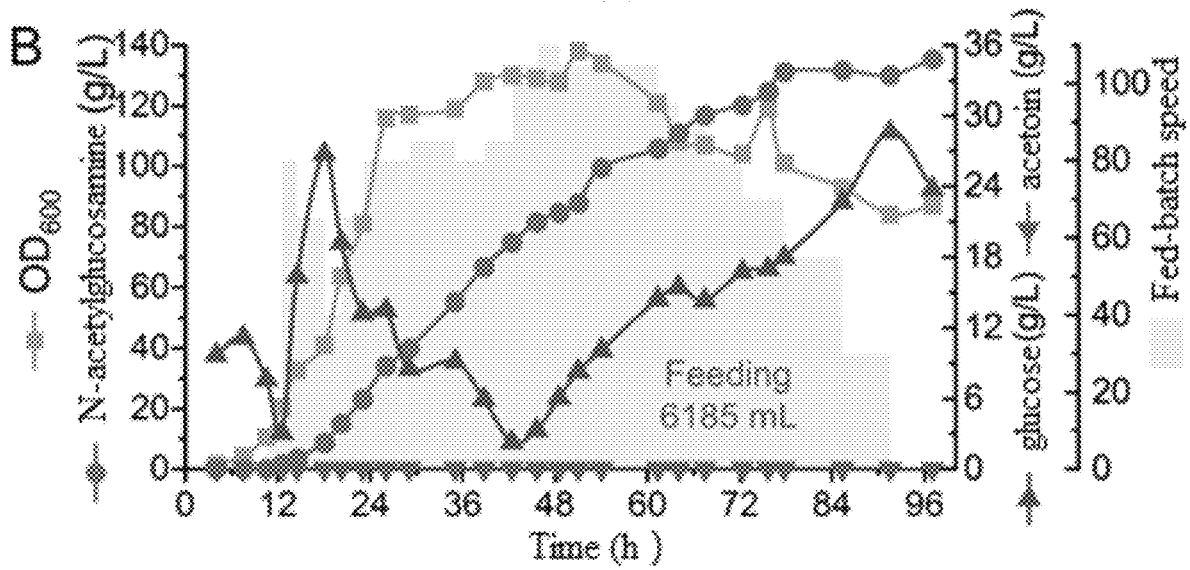

FIG. 6 shows the results of fed-batch fermentation in a 15 L tank with BNDR122.

DETAILED DESCRIPTION OF THE PREFERRED EMBODIMENTS

Seed culture medium (g/L): tryptone 10, powdery yeast 5, and NaCl 10.

Fermentation medium (g/L) in shake flask: tryptone 6, powdery yeast 12, urea 6, $K_2HPO_4 \cdot 3H_2O$ 12.5, $KH_2PO_4$ 2.5, $CaCO_3$ 5, and trace element 10 ml/L, where the solution of trace elements comprises, by g/L, $MnSO_4 \cdot 5H_2O$ 1.0, $CoCl_2 \cdot 6H_2O$ 0.4, $NaMoO_4 \cdot 2H_2O$ 0.2, $ZnSO_4 \cdot 7H_2O$ 0.2, $AlCl_3 \cdot 6H_2O$ 0.1, $CuCl_2 \cdot H_2O$ 0.1, and $H_3BO_4$ 0.05, and 5M HCl.

Fermentation medium (g/L) in fermenter: tryptone 20, powdery yeast 20, urea 10, $K_2HPO_4 \cdot 3H_2O$ 12.5, $KH_2PO_4$ 2.5, $CaCO_3$ 5, and trace element 10 ml/L, where the solution of trace elements comprises, in g/L, $MnSO_4 \cdot 5H_2O$ 1.0, $CoCl_2 \cdot 6H_2O$ 0.4, $NaMoO_4 \cdot 2H_2O$ 0.2, $ZnSO_4 \cdot 7H_2O$ 0.2, $AlCl_3 \cdot 6H_2O$ 0.1, $CuCl_2 \cdot H_2O$ 0.1, and $H_3BO_4$ 0.05, and 5M HCl.

Determination method of acetylglucosamine: High performance liquid chromatography (HPLC): Agilent 1260, RID detector, HPX-87H column (Bio-Rad Hercules, CA), mobile phase: 5 mM $H_2SO_4$, flow rate 0.6 mL/min, column temperature 35° C., and volume of injection: 10 μL.

Example 1: Construction of GlcN6P Responsive Element

Figure 1:
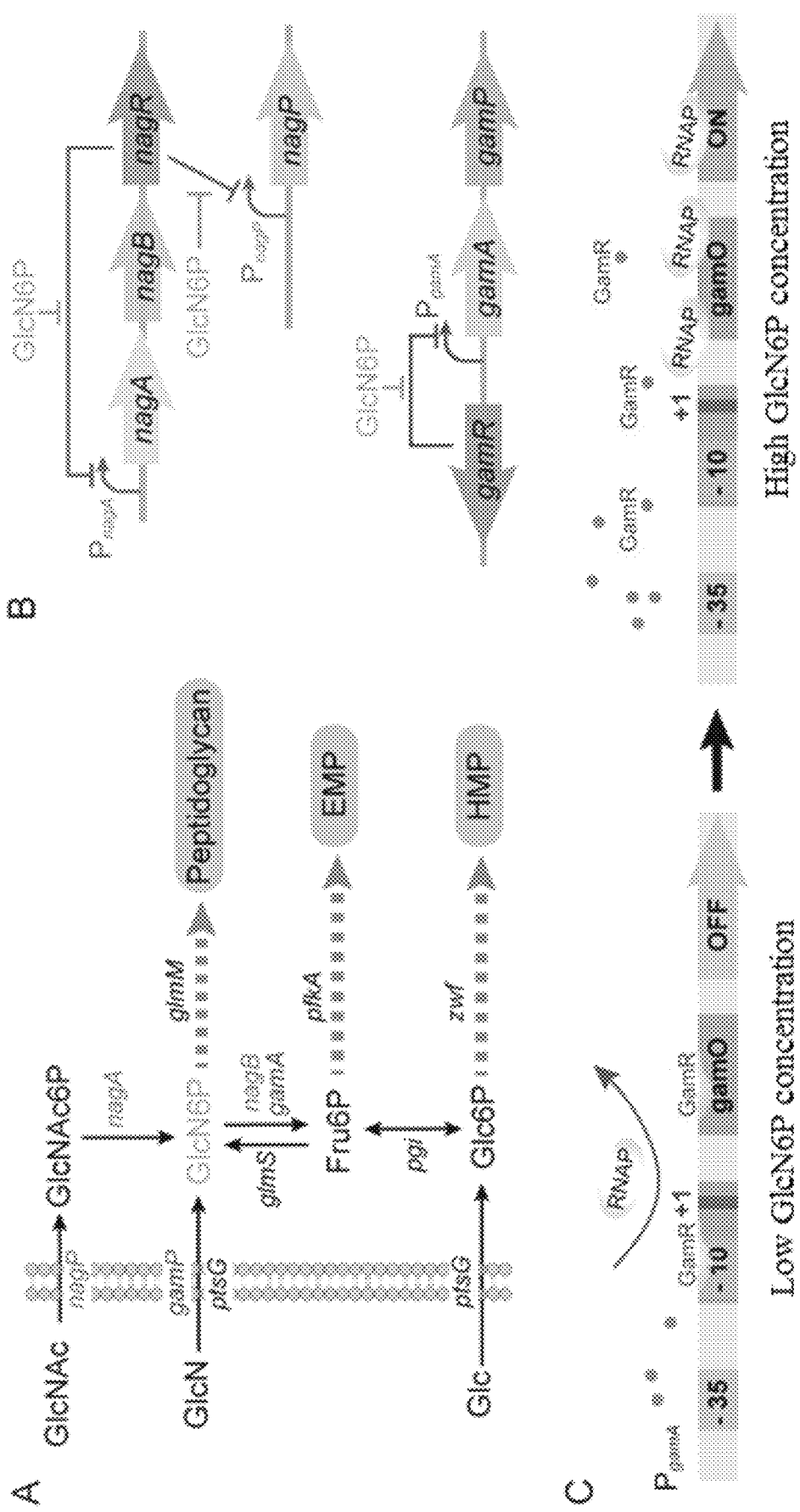
FIG. 1 shows the principle underlying regulation of related genes by GlcN6P.

Working mechanism of the present invention: In *Bacillus subtilis*, glucosamine 6-phosphate (GlcN6P) is an important metabolic regulator. When glucose is used as a carbon source, its intracellular concentration is amenable to feedback regulation mediated by glmS riboswitch. When glucosamine (GlcN) or N-acetylglucosamine (GlcNAc) is used as a carbon source, GlcN6P activates the expression of operons related to the catabolism of these two carbon sources, respectively. This process is achieved with transcription factor GamR or NagR (FIG. 1). The principle of regulation on GamR is shown in FIG. 1C. GamR can recognize and bind to a specific site (gamO) on the promoter $P_{gamA}$ to prevent the binding of RNA polymerase and the initiation of transcription. When the intracellular GlcN6P concentration is higher than its response threshold, RNA polymerase will bind to gamO and change its structure so that GamR cannot bind to the promoter $P_{gamA}$, and transcription can proceed normally (Gaugue, I., Oberto, J., Plumbridge, J., 2014. Regulation of amino sugar utilization in *Bacillus subtilis* by the GntR family regulators, NagR and GamR. Mol. Microbiol. 92, 100-115. doi.org/10.1111/mmi.12544). Therefore, this regulatory system can be used for engineering and to realize automatic regulation of N-acetylglucosamine and its main competitive pathways, thereby promoting the continuous and efficient flow of glucose to the synthesis of N-acetylglucosamine.

The GlcN6P responsive element constructed in the present invention includes the transcription factor GamR and a promoter containing a GamR binding site, where part of the sequence of the promoter containing a GamR binding site is shown in FIG. 2A. The mechanism of regulation of the responsive element by intracellular GlcN6P is shown in FIG. 1C. When the concentration of GlcN6P is low, GamR binds to the promoter containing a GamR binding site, which limits the transcription of a downstream gene. As the concentration of GlcN6P increases, the binding between GamR and the promoter becomes weaker, so the transcription of the downstream gene is gradually enhanced.

To construct responsive elements of different abilities, a series of hybrid promoters containing a GamR binding site (having a nucleotide sequence as shown in SEQ ID NO: 6-SEQ ID NO: 19) were designed, and ligated to a vector containing a green fluorescent protein after synthesis. Also, the gamR gene in the wild-type *Bacillus subtilis* 168 (BS168) was knocked out to obtain a recombinant strain BS01(BS168ΔgamR), and the plasmids including a hybrid promoter above were respectively transformed into BS168 and BSO1, respectively. The expression of the promoters before and after GamR binding was verified.

FIG. 2B shows the change in expression of various hybrid promoters when GamR is expressed or deleted. Among these promoters, the expression of $P_{vg6}$, $P_{gamA}$, and $P_{sg2}$ changes by 2.4, 5.7, and 11.9 times before and after GamR binding, respectively. To further verify the response of these three promoters to GlcN6P, relevant genes nagB and gamA allowing GlcN6P to enter the glycolysis pathway were knocked out in BSO1 to obtain the recombinant strain BSO3 (BS168ΔgamRΔnagBΔgamA). In this way, different concentrations of GlcN could be added to control the concentration of intracellular GlcN6P. By using the regulation mechanisms shown in FIGS. 3A and 3B, the activation and inhibition of genes mediated by GlcN6P responsive elements were verified. When activation is verified, GamR and a promoter containing a GamR binding site were both positioned on the same vector, and the effect of the addition amount of GlcN on the promoter expression was verified by GFP. $P_{vg6}$, $P_{gamA}$, and $P_{sg2}$ enhance with the increase of the addition amount of GlcN, reach the maximum when the amount of addition is 1 g/L, and will not increase any more when the concentration exceeds this concentration. The expression levels of these three promoters are at about 1:3:4. When inhibition is verified, the repressor XylR and xylose-inducible promoter on pLCx-dCas9 were respectively replaced by gamR and $P_{vg6}$, gamR and $P_{gamA}$, and gamR and $P_{sg2}$, to obtain the vector pLCv-dCas9, pLCg-dCas9, and pLCs-dCa9. The three vectors were linearized with Eco91I and transformed into B503, and then GFP-specific sgRNA expression vector psga-GFP (having a nucleotide sequence as shown in SEQ ID NO:20)linearized with Eco31I and a plasmid with constitutively expressed GFP were transformed to obtain the strain BS13, BS23 and BS33. The expression of fluorescent protein was measured by adding GlcN. The inhibition also increases with the increase of the addition amount of GlcN, and the weakening effect of the three promoters is also $P_{vg6} < P_{gamA} < P_{sg2}$. As shown in FIG. 3C, the green fluorescent protein (GFP) and red fluorescent protein (mCherry) are used to verify the effects of simultaneous activation and inhibition of GlcN6P responsive element.

Example 2: Regulation of GlcNAc Synthesis by GlcN6P Responsive Element

To regulate the GlcNAc synthesis by using the constructed GlcN6P responsive element, the gamR gene in recombinant *Bacillus subtilis* BSGNY-$P_{veg}$-glmS-$P_{43}$-GNA1 constructed in Patent Publication No. CN107699533A was knocked out, to obtain the recombinant strain BNDR000. The vector pLCg-dCas9 (having a nucleotide sequence as shown in SEQ ID NO: 3) and paga-zpg (having a nucleotide sequence as shown in SEQ ID NO: 7 in Patent Publication No. CN108148797A) were linearized with endonuclease Eco91I and transformed into BNDR000 to obtain BNDR020. The GNA1 expression vector pSTg-GNA1 (having a nucleotide sequence as shown in SEQ ID NO: 1) regulated by $P_{gamA}$ was transformed into BNDR020 to obtain the recombinant strain BNDR022. Finally, the key gene alsSD responsible for the synthesis of by-product acetoin was knocked out to obtain the recombinant strain BNDR122.

Example 3: Fermentation Production of Acetylglucosamine with Recombinant Bacillus subtilis BNDR122

The recombinant Bacillus subtilis BNDR022 constructed in Example 2 was used for shake-flask fermentation. Bacillus subtilis BSGNY-$P_{veg}$-glmS-$P_{43}$-GNA1 was used as a control, and was cultured and fermented under the same conditions. The seed cultured at 37° C. and 220 rpm for 12 h was inoculated into a fermentation medium at an inoculation amount of 5%, and cultured at 37° C. and 220 rpm for 60 h. The GlcNAc content in the final fermentation supernatant reaches 28.0 g/L, which is 53.0% higher than that produced by the starting strain (BSGNY-$P_{veg}$-glmS-$P_{43}$-GNA1). Moreover, the yield of N-acetylglucosamine by fermentation with the recombinant Bacillus subtilis provided in the present invention is increased from 0.244 g/g glucose to 0.373 g/g glucose, but the strain BNDR still produces 10 g/L of by-product acetoin. To eliminate the production of acetoin, alsSD, a key gene responsible for acetoin synthesis, was knocked out to obtain the recombinant strain BNDR122, which was verified in 15 L fermenter. The seed cultured at 37° C. and 220 rpm for 12 h was inoculated into a fermentation medium in a fermenter at an inoculation amount of 5%, and cultured in a 15 L fermenter at 37° C. and pH 7.0, where the rate of aeration was 1.5 vvm, and the rotational speed was controlled to 500-900 rpm to maintain dissolved oxygen at 30% or higher. The initial liquid volume was 7.5 L, and glucose of 750 g/L was continuously added to control the glucose concentration between 1-30 g/L. The final acetylglucosamine content in the fermentation supernatant reaches 131.6 g/L, which is the highest level of fermentation production at present, and lays a foundation for its industrialization.

Comparative Example 1: Regulation of GlcNAc Synthesis by Different GlcN6P Responsive Elements In the method of the present invention, the GlcN6P responsive element was used to enhance the key gene GNA1 responsible for GlcNAc synthesis, and the key genes zwf, pfkA and glmM in the main competition pathways were weakened (FIG. 4A), thereby promoting the recombinant Bacillus subtilis to continuously synthesize GlcNAc efficiently with glucose. In the present invention, three GlcN6P responsive promoters $P_{vg6}$, $P_{gamA}$, and $P_{sg2}$ of different expression levels were obtained. In the recombinant strain BNDR122, the enhancement and weakening are both regulated by the promoter $P_{gamA}$ with a moderate expression level among the three promoters. In order to compare the effects of promoters of different expression levels, the vectors pLCs-dCas9 (where the $P_{gamA}$ promoter in the vector pLCg-dCas9 was replaced by $P_{sg2}$) and pLCv-dCas9 (where the $P_{gamA}$ promoter in the vector pLCg-dCas9 was replaced by $P_{vg6}$) were integrated with dCas9 expressed by $P_{sg2}$ and $P_{vg6}$. The vectors pSTs-GNA1 (where the $P_{gamA}$ promoter in the vector pSTg-GNA1 was replaced by $P_{sg2}$) and pSTv-GNA1 (the $P_{gamA}$ promoter in the vector pSTg-GNA1 was replaced by $P_{vg6}$) that use $P_{sg2}$ and $P_{vg6}$ to regulate the expression of GNA1 were transformed. FIGS. 4B-4E show the results of enhancement and weakening using combinations of promoters with different expression levels. Only when the enhancement and weakening are both carried out using the promoter $P_{gamA}$ of moderate expression level, the GlcNAc production is the highest and reaches 28.0 g/L.

Comparative Example 2: Effect of Knockout of Acetoin Synthesis Pathway

Compared with BNDR022, BNDR122 causes no accumulation of by-product acetoin. In order to compare the effect of knocking out the key gene alsSD responsible for acetoin synthesis, fed-batch fermentation was carried out with BNDR022 and BNDR122 in a 15 L fermenter. The results of fermentation are shown in FIGS. 5 and 6. The by-product acetoin produced by BNDR022 can finally reach 22.9 g/L, and the GlcNAc production can reach 96.3 g/L. In contrast, the GlcNAc production of BNDR122 can reach 131.6 g/L, and no by-product acetoin is produced. This not only lays a foundation for further fermentation production therewith, but also is more conducive to the subsequent separation and purification process.

While the present invention has been described above by way of preferred examples, the present invention is not limited thereto. Various modifications and changes can be made by those skilled in the art without departing from the spirit and scope of the present invention as defined by the appended claims.

What is claimed is:

1. A method for promoting N-acetylglucosamine synthesis, comprising controlling the expression of glucosamine 6-phosphate N-acetyltransferase GNA4 by GNA1 by using a GlcN6P responsive element to dynamically regulate the N-acetylglucosamine synthesis pathway; and using the GlcN6P responsive element to regulate a compound formed by binding a dCas9 protein to three sgRNA expression fragments acting on zwf, pfkA and glmM genes, to dynamically weaken the glycolysis pathway, the pentose phosphate pathway and the peptidoglycan synthesis pathway, wherein the GlcN6P responsive element comprises the transcription factor GamR and a promoter containing a GamR binding site, where the transcription factor GamR has an amino acid sequence comprising positions 1-235 of an amino acid sequence deposited under NCBI Accession No.: WP_015382651.1, and the promoter is a $P_{gamA}$ promoter or a hybrid promoter constructed by adding a GamR binding site to a constitutive promoter.

2. The method according to claim 1, wherein the promoter $P_{gamA}$ has the nucleotide sequence of SEQ ID NO: 5.

3. The method according to claim 1, wherein the glucosamine 6-phosphate N-acetyltransferase GNA1 has the amino acid sequence of SEQ ID NO: 2.

4. The method according to claim 3, wherein the vector pSTg-GNA1 is used as an expression vector of glucosamine 6-phosphate N-acetyltransferase GNA1, and the vector pSTg-GNA1 has the nucleotide sequence of SEQ ID NO:1.

5. The method according to claim 1, wherein the vector pLCg-dCas9 is used as an expression vector of the dCas9 protein, and the vector pLCg-dCas9 has the nucleotide sequence of SEQ ID NO: 3.

6. The method according to claim 1, wherein the method further comprises knocking out the key gene alsSD for the synthesis of by-product acetoin.

7. The method according to claim 6, wherein the key gene alsSD is knocked out by transforming an alsSD knockout frame having the nucleotide sequence of SEQ ID NO: 4.

8. A recombinant *Bacillus subtilis*, wherein a GlcN6P responsive element is used to control the expression of glucosamine 6-phosphate N-acetyltransferase GNA1 to dynamically regulate the N-acetylglucosamine synthesis pathway; and the GlcN6P responsive element is also used to regulate a compound formed by binding a dCas9 protein to three sgRNA expression fragments acting on zwf, pfkA and glmM genes, to dynamically weaken the glycolysis pathway, the pentose phosphate pathway and the peptidoglycan synthesis pathway, wherein the GlcN6P responsive element comprises the transcription factor GamR and a promoter containing a GamR binding site, where the transcription factor GamR comprises positions 1-235 of an amino acid sequence deposited under NCBI Accession No.:

WP_015382651.1, and the promoter is a $P_{gamA}$ promoter or a hybrid promoter constructed by adding a GamR binding site to a constitutive promoter.

9. The recombinant *Bacillus subtilis* according to claim 8, wherein *Bacillus subtilis* BSGNY-$P_{veg}$-glmS-$P_{43}$-GNA1 is used as a starting strain, and the starting strain is based on *Bacillus subtilis* 168 in which the genotype was engineered as follows: ΔnagPΔgamPΔgamAΔnagAΔnagBΔldhΔptaΔglcKΔpckΔΔpyk::lox72; and the promoter $P_{veg}$ is used to regulate the expression of the phosphatase yqaB from *E. coli* and the glmS of *Bacillus subtilis* 168, and the promoter $P_{43}$ is used to regulate the expression of GNA1.

10. A method for producing acetylglucosamine, comprising fermentation of the recombinant *Bacillus subtilis* strain according to claim 8.

11. The method according to claim 10, wherein the method comprises inoculating the seed of the recombinant *Bacillus subtilis* strain cultured at 35-39° C. and 200-220 rpm for 10-15 h into a fermentation medium in a shake flask at an inoculation amount of 1-10%, and culturing at 35-39° C. and 200-220 rpm for 50-70 h.

12. The method according to claim 10, wherein the method comprises inoculating the seed of the recombinant *Bacillus subtilis* strain cultured at 35-39° C. and 200-220 rpm for 10-15 h into a fermentation medium in a fermenter at an inoculation amount of 1-10%, and culturing in the fermenter with a liquid volume of 30-50% at 35-39° C. and pH 6.5-7.5, where the rate of aeration is 1-2 vvm, the rotational speed is controlled to 500-900 rpm to maintain dissolved oxygen at 30% or higher, and glucose of 750 g/L is continuously added to control the glucose concentration between 1-30 g/L.

13. The method according to claim 10, wherein the method comprises promoting N-acetylglucosamine synthesis in the fields of food, pharmaceuticals, nutraceuticals and health products, or cosmetics.

* * * * *